(12) United States Patent
Romano et al.

(10) Patent No.: US 8,888,753 B2
(45) Date of Patent: Nov. 18, 2014

(54) DISPOSAL CHAIN SUPPLY SYSTEMS METHOD AND APPARATUS

(75) Inventors: Jack W. Romano, Kirkland, WA (US); Adam L. Smith, Palm Desert, CA (US)

(73) Assignee: Medindica-Pak, Inc., Kirkland, WA (US)

( * ) Notice: Subject to any disclaimer, the term of this patent is extended or adjusted under 35 U.S.C. 154(b) by 513 days.

(21) Appl. No.: 13/348,074

(22) Filed: Jan. 11, 2012

(65) Prior Publication Data
US 2012/0109055 A1 May 3, 2012

Related U.S. Application Data

(63) Continuation of application No. 11/378,078, filed on Mar. 17, 2006, now Pat. No. 8,118,795.

(60) Provisional application No. 60/664,050, filed on Mar. 22, 2005.

(51) Int. Cl.
*A61M 1/00* (2006.01)

(52) U.S. Cl.
CPC ........... *A61M 1/0001* (2013.01); *A61M 1/0023* (2013.01); *A61M 1/0017* (2013.01)
USPC .......................................... 604/319; 604/403

(58) Field of Classification Search
CPC ............ A61M 1/00; A61M 5/44; A61B 5/20; A61B 10/00; A61F 5/44; A61F 5/45; A61G 9/00; A61G 9/006; A61J 1/10; A47K 11/12
USPC ......... 604/317–319, 321, 403; 4/144.1–144.3
See application file for complete search history.

(56) References Cited

U.S. PATENT DOCUMENTS

| | | | |
|---|---|---|---|
| 3,032,037 A | 5/1962 | Huber | |
| 3,661,143 A | 5/1972 | Henekin | |
| 4,178,976 A | 12/1979 | Weiler | |
| 4,388,922 A | 6/1983 | Telang | |
| 4,397,643 A | 8/1983 | Rygel | |
| 4,620,846 A | 11/1986 | Goldberg et al. | |
| 4,655,197 A | 4/1987 | Atkinson | |
| 4,886,504 A | 12/1989 | Arvidson et al. | |
| 4,976,707 A | 12/1990 | Bodicky et al. | |
| 5,269,924 A | 12/1993 | Rochat | |
| 5,364,384 A | 11/1994 | Grabenkort | |
| 5,382,244 A | 1/1995 | Telang | |
| 5,514,123 A | 5/1996 | Adolf | |
| 5,586,973 A | 12/1996 | Lemaire et al. | |
| 5,899,349 A | 5/1999 | Moore | |
| 6,318,417 B1 | 11/2001 | Davis | |
| 6,492,332 B1 * | 12/2002 | Demopulos et al. | ......... 514/17.4 |
| 6,942,123 B2 | 9/2005 | Wertenberger | |

(Continued)

*Primary Examiner* — Melanie Hand

(57) ABSTRACT

This patent application teaches methods and apparatus of an efficient disposal chain system which includes a process of receiving fluid enclosing containers, transforming said containers into collection containers by integrating said containers into vacuum canister collection systems. Such a collection system includes a remote vacuum source configured to draw a vacuum force away from said container and towards said container. Such a vacuum source is configured to draw room air. Such a force is configured to draw waste materials along a path towards said collection container. A transformation of said containers includes deriving said containers from supply chains and transforming said containers into said collection systems at least in part by supporting said containers inside said canisters from below utilizing various configurations of measurement stands, said stands configured to support and accommodate various sizes, types and shapes of said containers.

21 Claims, 23 Drawing Sheets

(56) References Cited

U.S. PATENT DOCUMENTS

| | | |
|---|---|---|
| 7,185,681 B2 | 3/2007 | Romano |
| 7,329,250 B2 | 2/2008 | Romano et al. |
| 7,798,181 B2 | 9/2010 | Romano |
| 7,854,729 B2 | 12/2010 | Romano et al. |
| 7,931,629 B2 | 4/2011 | Romano |
| 2002/0128584 A1 | 9/2002 | Brown et al. |
| 2002/0128612 A1 | 9/2002 | Andersson |
| 2003/0132249 A1 | 7/2003 | Romano |
| 2004/0122383 A1 | 6/2004 | Romano et al. |
| 2004/0149348 A1 | 8/2004 | Wertenberger |
| 2005/0215961 A1 | 9/2005 | Romano et al. |
| 2006/0217674 A1 | 9/2006 | Romano et al. |
| 2008/0132855 A1 | 6/2008 | Romano et al. |
| 2009/0057347 A1 | 3/2009 | Leys |
| 2010/0326565 A1 | 12/2010 | Romano |

\* cited by examiner

DISPOSAL CHAIN SUPPLY SYSTEMS METHOD AND APPARATUS

CROSS REFERENCE TO RELATED APPLICATION

Under 35 USC 120, this Patent Application is a continuation of U.S. patent application Ser. No. 11/378,078 filed on Mar. 17, 2006 which claims priority under 35 USC 119 from U.S. Provisional Patent Application Ser. No. 60/664,050 which was filed on Mar. 22, 2005.

FIELD OF THE INVENTION

This invention relates to the field of reducing the waste stream burden in the medical field, but not limited to that.

BACKGROUND OF THE INVENTION

In particular, this application relates to systems used in the collection and disposal of certain medical wastes. The collection of fluent waste material is a common procedure in the medical field. Most methods of surgical waste collection are carried out using vacuum suction. Some methods use gravity, while some use impelling devices which produce suction vacuum. Examples of such impelling devices may comprise a meniscus shaver, a lipo-suction system, an arthroscopic fluid pump, a tissue ablator, an endoscopic irrigation and aspiration wand and the like. Surgical fluid waste is collected in containers commonly referred to as canister and/or canister liners. These waste collection devices are generally disposable; some are re-cycled, re-processed, or rewashed. Some collection devices are re-used. Some are partially reused while some are intermittently re-used. Some are disposable or partially disposable. Some are used in conjunction with servicing units while some are used with additive agents for treating the waste material. Some are used multiple times on multiple patients without the preferable cleaning in between treatment of different patients. In certain instances reused devices are cleaned, reprocessed, sterilized, re-sterilized and or recycled and or prepared for reuse. There are disadvantages to the use of disposable collection canisters and canister liners. One problem is that disposable collection canisters and disposable collection liners contribute contaminated infectious plastic waste to the medical waste stream which is undesirable for the environment. Reuse of disposable collection devices by recleaning or reprocessing or recycling and or sterilizing, has the disadvantages of adding costly labor and requiring additional labor costs for sorting, containing, transporting, and, handling of contaminated medical waste containers, and then the added costs of product re-entry into the internal/external product re-sterilization internal/external distribution system. There is a significant need to reduce medical waste. The need to reduce medical waste is a serious common goal of the United States and Internal Agencies. The Environmental Protection Agency (EPA) and the American Hospital Association has entered into a landmark Memorandum of Understanding (MOU) formally establishing the goals to reduce medical waste 50% by the year 2010. Hospitals for Healthy Environment (www.H2E-Online.org) is the name of the aforementioned alliance for waste reduction, supported by formidable organizations and companies such as the American Nurses Association, Healthcare Without Harm, the EPA, plus Group Purchasing Organizations, leading health care organizations, federal, state and local government agencies, and health care associations and the like.

Description of the Prior Art

It is important in the health care field to have good quality sturdy and reliable products. This is true especially in the field of collection of contaminated biological waste material. Containers for these purposes must be easy to use, and be designed with good human factors and ergonomics for the operators of such devices. One key important ergonomic feature is that the systems for collection of biological waste must be easy to use, and the amount of effort and strength required to assemble such systems should be easy and require little effort by the operators. The instant embodiments of the instant case provide for such ease of use. In addition other useful features which represent good quality standards for collection containers and systems and methods involve stability so that when containers are placed on a horizontal surface they are stable. The container should be puncture, leak and impact resistant and be stable and secure when dropped. It should be manufactured out of materials which function for the intended purposes, and if made form a polymer, have a durometer which should not crack or break if dropped. Labels and brackets should be made durable. The system should be autoclavable so that if desired by the customer it may be reused. The systems should be available in various sizes to accommodate a variety of patient populations as well as be effective to operate in a number of different treatment situations and locations. The system should not have any parts that are sharp, that might compromise the operator's personal protection, and not tear gloves, or other personal protective equipment such as gowns, gloves, masks, etc. Designs of systems of this sort should promote safe clinical care and perform according to those safe clinical standards. The design should promote resistance to opening after final sealing for disposal, as well as promote easy assembly and easy opening (in this case easy sealing and unsealing) with good ergonomic and human factor attributes. All closure seals should function tightly and maintain the leak proof seal during use, handling and transport. The design should accommodate easy carrying and handling so that transport of the systems may be done safely without contaminating the surrounding environment. Grips and handles should be designed for ease of access and use. Parts should be designed for ease of decontamination, and be rugged to withstand multiple autoclaving if desired. Openings must be free of obstruction, entanglement and sub-assembly parts must be able to attach and dis-attach without requiring undue hand work or significant effort.

In addition various scenarios that occur during health are supply chain efficiency and supply management require unique features to products that encounter such scenarios. Some scenarios occur in the operating room. For example, in collection systems that should be designed to be easy to use during room turnover. They should be easy to use during intra-operative system changing. They should be easy to use after terminal sterilization and room setup. And they should be easy to use when preparing an operating room at the beginning of the operating day. Such collection systems should be easy to check/test to make sure they are operating correctly. Especially in a vacuum suction collection system, testing suction and checking seals must be easy and without undue fiddling or parts manipulation. This is especially significant whereas many times the individual who may be preparing the collection system for use, may do so prior to and at times different than actual use, which means the operator setting up the system for use is not the same operator using the system to collect waste. Ease of checking/testing, especially of the seals becomes important if, for example the prior individual does not properly assemble or prepare the system for subsequent use and the operator must then insure the system is in intended working condition at a later time. It is also desirable, when dealing with contaminated biological waste that minimum handling of unsealed containers holding biological waste material is kept to a minimum, and that containers are sealed prior to handling and transport. It is also important that a minimum of handling be required during the various scenarios mentioned above, and, that hand and eye coordination may be achieved to carry out the aforementioned clinical safety features. It is understood that the aforesaid features for the aforesaid scenarios do not only apply to the operating room. Other settings as further defined by the instant application are all applicable. Another example is that safe sealing of containers containing biological waste must be achievable with one handed technique as provided by the instant system. The feature of creating a stand 3, that has different dimensions from a system centerline so that cap 15 may be placed on a container 14 having waste material therein provides a good clinically safe procedure. This sealed bottle is then removed with one hand, and replaced with an empty container while the other hand is occupied holding lid 4. The container stand/container relationship provides for anti rotation of the stand while cap 15 is securely threaded down to seal the container holding the biological waste material. These practical features bring good ergonomic and human factors to the instant system while providing a good clinically safe system into the health care setting.

Certain disadvantages of the prior art in these regards will become better understood with the explanations of the following references. U.S. Pat. No. 5,792,126 to Tribastone, et. Al., discloses a collection canister system comprising canister interior of preferably 5000, 10000, and 15000 cubic centimeters and taught to be effective for all procedures. A container of this size has disadvantages because it is too big for many collection applications. For example, suction collection for anesthesia where it is convenient to have a small collection canister attached to an anesthesia machine is preferable, especially in that most anesthesia suction volumes constitute just a few cubic centimeters of sputum or pharyngeal throat saliva most of the time. Larger equipment is also inconvenient in smaller rooms where suction collection equipment is found such as in the emergency room, the intensive care unit, the coronary care unit, patient hospital rooms, the neo-natal infant care units, physician offices, physician owned surgery suites, physician office surgery and procedure rooms, outpatient surgery centers, ambulatory surgery centers, ambulances and other rooms beside operating rooms which require smaller apparatus for smaller more confined spaces. There are also concerns with cross contamination in any system where contaminated waste material remains in a room during the presence of subsequent multiple patients. Another disadvantage of the larger 5000, 10000, 15000 cc containers is weight and mobility. Such weight in the extremely large heavy volumes are sometimes difficult ergonomics, imposing risk of injury to personnel such as back pain, and other injuries whereby by seams in floors and door jams which are not smooth may induce tipping over and spillage of large volumes of medical waste. Another disadvantage of such large heavy containers is its size. Such large container are more difficult to keep clean and cumbersome to handle, and because of the awkward size could cause ergonomic strain as related to the U.S. Pat. No. 5,792,126 reference. U.S. Pat. No. 5,960,837 to Cude et. Al., discloses a suction canister and in combination whereby only a destructive force will separate the parts which renders the Cude invention to be an only disposable product which is costly whereby each time a canister is used another is purchased to replace it. A purchase is made and is costly to the customer and each plastic disposable product enters the disposal chain waste stream and another piece of garbage enters the land fills or incinerators which are disadvantages. This is expensive, and requires ongoing inventory space, and inventory handling which are at a premium. Another disadvantage is a lack of choice for the customer to re-process, re-sterilize or re-use, which options are beneficial but not available with the U.S. Pat. No. 5,960,837 reference. U.S. Pat. No. 5,901,717 to Dunn et. Al., discloses a canister and flushing system. This system comprises a complex system for handling a collection canister. These disadvantages of this system are that expensive equipment is required and it is complex equipment. The expenses and maintenance, plus required periodic inspection by biomedical engineering increases labor costs associated with its presence. In addition the equipment must be kept clean which is additional requirement for daily operations. Other disadvantages of a reusable canister which requires costly labor for internal processing, reprocessing, resterilization and reusing. In most institutions, volume of such collection systems is quite high imposing internal/external processing costs. The system discloses the disposable flush kit which maintains higher disposable costs along with the higher costs associated with internal distribution, inventory handling and higher disposable waste removal costs. U.S. Pat. No. 4,419,093 to Deaton discloses a reusable canister having a disposable lid and liner. This system is delivered in pieces and requires subassembly by the customer prior to operation. This requires additional labor which is costly and involves the inventory tracking of a plurality of pieces to a system in sets, and often times lids and liners can become separated and when out of numeral matching balance one cannot be use with out the other, whereas resulting in an incomplete set and a unusable subassembly. This disadvantage complicates the ongoing internal/external distribution and tracking of pieces which adds costly labor, inventory management and excess handling. The U.S. Pat. No. 4,419,093 reference also discloses contribution of garbage to the waste stream which is a serious environmental concern. Other disadvantages of disposable collection containers include the difficulty in which to assemble a lid to a container body. Many disposable canister systems have a container body which is stackable. This stack ability allows the container bodies to be nested on each other with one container resting substantially within the other, with the exception of about one to two inches of body length. This stack ability feature is desirable whereas the volume of containers handling in the disposable application is very high. For example a busy institution may process anywhere between 10,000 and 50,000 disposable canisters per year. The stack ability feature makes these canisters easier to transport in volume. One problem with the assembly of such stackable canister and it's associated lid, is that the snap on feature of lid must be very tight in order to be fluid leak proof in the event of tip over. In order for these canister lid interfaces to be leak proof they must fit very tightly making for a very difficult assembly. The force required to assemble the canister and lids of this nature is greater that a force which would normally be deemed easy to use. In fact they are very difficult to use. Good ergonomic systems include assembly and dis-assembly features that do not require undue finger, hand and/or upper body strength. Many of the prior art collectin systems have snap together features that, due to their seal design, require more force to assemble, than most operators can provide. This is because of the force required to snap together the seals that =are not meant to come apart, and that must be tight enough to stay sealed during transport, handling and tipping over. The applicant believes that if a system cannot be assembled with much less force and upper body strength of the average operator, then there are human factors and ergonomics design issues that are solved by the instant case. The applicant believes that the snap fit force utilized to keep a lid and canister housing together during transport and tippage is not the same force that provides for good human factor/ergonomic and good clinical handling. Applicant contents that when snap fit forces are greater than the average upper body strength of the average operator, then clinical safety is in jeopardy and personal protective equipment such as protective gloves are at risk for tearing or a hole.

Description of the Invention

The instant embodiments provides methods and apparatus for utilizing fluid enclosing product transfer delivery container which do not embody the self inherent physical construct capacity to maintain shape under extreme negative vacuum pressures up to negative minus 1 atmospheres. Examples of cost effectively fabricated fluid enclosing containers made for delivery of fluids which may not embody inherent implosion resistant structural strength and rigidity needed for suction vacuum collection, may include plastic delivery containers such as plastic pour bottles and intravenous containers. The present invention discloses cost effective practical solutions for reducing waste, reducing labor, reducing inventory, reducing the receiving, reducing the internal distribution, and reducing the inventory handling costs and the space required to carry inventory all involved with the collection waste materials. These achievements are carried out by the instant embodiments whereby successful suction vacuum collection may be realized using in a flexible, cost effectively fabricated, fluid enclosing distribution, commercialization, and transfer delivery containers. This patent application discloses collection systems that teach use of fluid enclosing product supply containers for collection, removal and disposal of waste material in the disposal chain. In particular, delivery containers for general distribution, transfer, and, administration of pour bottle solutions and intravenous solutions, parenteral and enteral solution containers and the like are converted into waste collection and disposal chain containers. This application also teaches use of a common fluid enclosing containers for both the supply and the disposal chain. The instant application also teaches use of containers found in inventory for supply and delivery of fluids, and then transforming them for the collection, removal, disposal, and for utility found in the deposal chain. This application teaches the use of a common fluid enclosing container for the product transfer and then integrates the container into systems for the collection and the removal of waste material. The instant application teaches waste reduction methods by integrating delivery containers fabrication with the collecting and disposing of waste materials. A few potential container fabrication methods applicable to the instant case comprise blow fill seal manufacturing, blow molding or continuous blow molding which produce an open top container. Another type of container fabrication process applicable to the instant application is a blow fill seal fabrication process commonly known and is a closed top manufacturing process whereby a container is formed, filled with fluid and hermetically closed within one machine. The instant application teaches the waste reduction methods by using manufacturing methods as mentioned such as blow molding, blow fill sealing, laminating sheets such as in intravenous solution container making methods to form enclosures. The purpose of the instant case is to transform these containers which are derived from a fluid delivery mode from product transfer and administration and the converting the container for the collection, removal, and disposal of waste materials. The embodiments of these instant case provdes container utility options for the transfer and administration of products, consumption of products, and for the waste collection removal and disposal options. The embodiments of this instant case discloses the utilization of fluid filled product transfer containers such as pour bottles and/or intravenous solution containers(IV bags) (and/or other product/ fluid containing enclosures used for intravenous therapeutics and the administration of anesthetic agents as well as other medicaments) for the receiving, collecting, containment and disposal of waste. Using fluid enclosing product distribution transfer/administration containers also for the handling of waste results in optimal reduction of waste, reduction of inventory, reduction in labor, reduction of internal/external inventory distribution/processing/re-processing/re-using/re-cycling, reduction of inventory handling and waste disposal costs( brought by the (unnecessary) the need for separate supply and disposal containers in certain circumstances), all are reduced by eliminating the supply chain costs with the fabrication of the said separate supply and disposal/collection containers. The question arises why pay for disposable container when a fluid delivery container can be derived from the supply side of the supply and disposal chains, and then be converted into a collection and removal/disposal container. Such containers are supplied clean/sterile and are made to meet certain sterility assurance levels (SAL). The instant embodiments confer options allowing consumer choices for the reduction of waste. Plastic transfer containers such as blow molded containers, continuous blow molded containers, blow fill seal containers, intravenous solution containers, containers made of laminated sheets of polymers, and of foils, are commonly used for the distribution transfer and administration of fluid products and other product such as sterile water, sterile saline solution intravenous solutions for IV therapeutics, IV solutions for administration of anesthetic agents and other water for injection (WFI) based fluid formularies as used in the medical field. Also included are cleaning solvents, prep solutions, alcohol solution and the like. Solutions used for intravenous therapeutics, parenteral administration, and administration of anesthesia, wound irrigation, irrigation for arthroscopic, endoscopic, laparoscopic procedures, irrigation for urology procedures and many other types of applications. The instant application names additional fluid materials delivered in polypropylene, and high density/low density polyethylene, and polyvinyl chloride containers which are all generally high volume supplies and or engage the supply chain on a just in time basis or on a vendor managed inventory managed basis or a customer managed basis for delivery and consumption. Intravenous solution containers are also used for the distribution/commercialization of these container products. It is understood the disclosed teachings of the instant case are not limited to sterile liquid distribution/supply containers or the transfer of fluid filled product containers. Other product transfer containers may be suitably integrated with innovation of the instant case, to function with the delivery and waste disposal capacity. Other container such as prep solution containers, alcohol containers, solvent containers, cleaning solution containers and the like, may function suitable within the scope of the present invention. These teaching are not intended to limit the attached claims below. Other product containers may also be used in the instant inventions. These product delivery containers are commercialized/distributed to the customer having volume cubic capacity sufficient in substantial proportion to the collection and the disposal of waste materials. The instant embodiments reduce the amount of plastic introduced to the waste stream.

The instant embodiments reduce the recycling, reprocessing and labor associated with the handling and re-use procedures thereby lowering the associated costs of waste removal. The instant embodiments reduce the supply chain costs from manufacturing to disposal. Collecting fluent waste material in fluid enclosing delivery containers such as open top blow molded, or continuous blow molded containers, intravenous solution containers or closed top blow fill seal containers which have been constructed and effectively fabricated with thin walls, which, do not have the strength or construction to resist high vacuum implosion forces. The instant case teaches options solving the disadvantages and problems of prior art containers. When the methods and apparatus embodied in the teachings of the instant application are utilized, the instant embodiments also provides for reducing the handing, reducing the labor and reducing the costly process of recycling, re-using, re-processing, sterilizing, and/or re-sterilizing. Certain product delivery transfer containers are fabricated, commercialized, and, are already present or in the supply, distribution, inventory, administration chain and/or in the customer facility. Present invention conveniently transforms, converts, and integrates these fluid enclosing transfer delivery containers for their transformation to waste materials collection containers creating a new type of environmental supply chain. We refer in part to this new novel environmental process as a disposal chain supply system, by the deployment of disposal chain supplies to collect, remove and dispose of waste material. This defines new supply and disposal chain systems, methods and apparatus for using fluid enclosing distribution containers and methods for processing systems from the clean delivery side of the fluid administration/consumption, into the dirty collection, removal, and disposal side integrating the disposal chain and the supply chain for environmental purposes, herein referred to as disposal chain supply systems. In essence disposal chain supply systems define a novel environmental process. In essence disposal chain supply systems are defined by transforming distribution containers into collection removal and disposal containers. In essence a disposal and supply container is an environmental conversion and transformation methods. In essence a disposal chain/supply chain container utilizing disposal chain supply chain systems confers options and advantages as disclosed by the instant case. In essence disposal supplies are environmentally preferred. In essence disposal supplying is the environmentally preferred method.

Difficulties exist with the use of certain containers when integrated into high negative pressure vacuum/suction system. Negative vacuum draw pressures at times up to minus one atmosphere of negative pressure, is common for drawing surgical waste materials from a surgical site into a collection receptacle. One problem is that the common blow molded or blow fill sealed containers are cost effectively manufactured with relatively thin plastic walls, sometimes down to a wall thickness range of .025 inches or less, and are generally made with a plastic materials such as high density polyethylene, polypropylene, polyvinyl chloride, or other like materials. Thin walled containers are commonly fabricated to reduce the plastic material mass (volume of plastic materials per unit) and hold down production costs and shipping weight. It is a common practice of container manufacturing to consume the minimum amount of material used per unit to fabricate each container yet maintain user function for cost effective manufacturing purposes. Common container material durometers comprising containers having such ranges of this wall thickness in these like materials are not generally strong enough to withstand the negative differential pressures of up to minus one atmosphere of negative pressure as commonly found in a vacuum/suction system without imploding or deforming. Product fluid enclosing distribution transfer containers, are commonly fabricated using processes know by artisans skilled in the arts of blow molding or continuous blow molding of open top containers and/or blow fill sealing of closed top containers as well as using such manufacturing processes such as thermal lamination of plastic sheet to form cavities/enclosures for the filling and production of intravenous solution containers and other parenteral containers and the like. The solution to the problem of implosion and bottle/container deformity which occurs under high vacuum pressure is to connect a container to a suction collection system whereby container wall is interposed between its inner chamber and an outer space with each space subjected to a common amount of negative draw vacuum force/pressure. This force envelops itself inside and outside of the container which forms opposing differential pressures which provides reinforcing balances by effecting a similar positive and negative neutralizing net force at the same time on the container wall eliminating negative implosion forces on the container wall. This is carried out by the container and canister of the instant case co-acting to contain waste and balance negative draw forces along the composite draw path. This addresses the issue of container deformity. This instant application discloses the neck of the pour bottle as the utilitarian area of the bottle for coupling with the lid of a canister system. The instant application discloses a throat aperture space (pour spout) of a plastic pour bottle as a utilitarian area for engagement of draw forces. The instant application discloses the throat space aperture, pour spout as a utilitarian area for coupling of a throat aperture plug. The instant application discloses a positive and negative exchange plug for providing communication between the draw force and the inside and outside of a fluid enclosing container. The instant application discloses locating an atmospheric pressure draw exchange at the neck of the container. The present application discloses interposing the container neck (pour spout) annularly between a plug and a lid for conversion coupling peripherally (not necessarily round). In an alternative embodiment a container neck cap is interposed between a bottle and a container neck and a canister lid cover. In still a further embodiment, a boss projecting downward off of a canister lid is interposed peripherally between a container neck and a container neck negative atmospheric draw force exchange plug. The present application discloses fabricating a blow molded container for delivery transformation and conversion and bayonet coupling (push and twist) to a canister system. It is understood the invention is not intended to be limited to bottle neck configuration which are round. Any shaped bottle/neck shape lid/cover cap, plug, and boss configuration suitable for arrangement/construction having structuration to carry out the utility of the present invention may be fabricated and deployed to a carry out the utility of the instant case. The present invention discloses positioning the plastic container throat space in a negative pressure draw vacuum system whereby an in draw force is disposed to transfer and deposit medical waste material into the container and an outdraw force is disposed to transfer the differential draw forces. The embodiments of the instant case utilizes the inner chamber of a plastic pour bottle as part of the pressure vacuum draw path. The present case discloses several embodiments for carrying out the invention. In one embodiment the container cap is shown guiding the exchanging forces and positioned along a negative vacuum force draw path at a locating along a site of waste material (surgical site/patient site) and a source from which the draw force emanates. The cap is connectable to a lid cover which is attached to a canister body. In a second embodiment a bottle neck is peripherally (not necessarily meaning round) interposed between a lid and a throat space. The pressure exchanger in the throat space, is disposed in the guiding position which exchange forces along a draw path at a location between a site of waste material and the source of vacuum draw.

Purpose and Methods of the Invention

One object of the invention is to position a liquid transfer fluid enclosing container upstream to a patient delivery sequence, and then place the container downstream in connection with the flow of a waste material. Another object of the invention is to convert a liquid container affecting egress of the liquid and then the positioning of the container in flow confining connection downstream to a source of waste material. Another object of the invention is to pour solution from a container and then place the container downstream along a vacuum draw path in flow control connection with a suction wand. Another object of the invention is to position a liquid transfer container upstream to and in vascular access connection with a patient and then position the transfer container downstream in flow control composite connection with a vacuum draw path.

Another object of the invention is to provide supply chain efficiency whereby the dispensing container is also the receiving receptacle/container. Another object of the invention is to provide the waste reducing processes whereby the egress of the container upstream from a healthcare patient is the same container positioned downstream in flow control association with a negative atmospheric pressure draw force and is then in flow confining connection with a suction wand. Another object of the invention is to provide practical steps for internal container handling including a) fabricating a transfer container, b) taking a transfer container and extending a draw path between a vacuum source and a suction wand, c) connecting a fluid enclosing delivery container to the path, d) depositing the waste material into the container. Another object of the invention is to provide methods and apparatus including a) enclosing a fluid in a container at manufacturing and transferring through distribution and administration for health care consumption, b) consuming at least a portion of the fluid product, c) converting the container into a vacuum collection system, d) removing the waste in the container e) disposing the waste. Another object of the invention includes a supply and disposal method comprising a) manufacturing a fluid enclosing container for the distribution, transfer and administration of a fluid product, b) consuming at least a portion of the liquid, c) directing a draw force to and from the container along a composite draw path, d) depositing waste material into the container.

Another object of the invention is to provide a method for reducing supplies comprising, a) providing a container fabricated for the delivery of a product, b) delivering the product, c) connecting the container to a vacuum source system, d) drawing waste material into the container, e) removing the waste material in the container, f) disposing of the waste material. Another object of the invention is to provide a method for reducing waste comprising a) transforming a waste receptacle from a container manufactured for enclosing and delivering a fluid, b) connecting the container to a composite waste draw conduit, c) depositing the waste material in the container, d) removing the container from the draw path, e) converting another delivery container into a waste receptacle comprising transformation of a fluid enclosing supply container into a waste collection receptacle. Another object of the invention includes a) providing the methods and apparatus for the transforming a plurality of supply containers into a plurality of waste containers. Another object of the invention is to enclose a plurality of supply containers having been transferred into a plurality of collection container within a single enclosure. Another object of the invention is to provide methods for transforming supplies into waste receptacles comprising a) constructing a fluid enclosing container, b) taking the container c) extending a draw path between a vacuum source and a suction wand d) connecting a delivery container to the path, e) depositing waste material into the container. Another object of the invention is to provide methods for deriving waste receptacles from supply containers including a) providing a liquid product in a selectively connectable waste receptacle b) disposing the receptacle in a vacuum collection container system, c) drawing a force along a composite draw path between a source of waste material and a vacuum source d) depositing waste in the delivery receptacle. Another object of the instant case comprises a) positioning a transfer container upstream in the flow of a patient care sequence for liquid dispensing and administration, b) positioning the container downstream in the flow of patient care in a material receiving and receptacle mode. Another object of the embodiments herein disclosed whereby the receptacle is positioned on the clean side of the supply and disposal chain for dispensing of it contents and the dispenser is position on the dirty side of the supply and disposal chain for receiving waste material as a receptacle, and this receptacle is in receiving structuration with a gravity flow system and or a composite vacuum draw path. Another object of the invention is to provide methods and apparatus for drawing a negative pressure within a transfer dispensing container. Another object of the invention is to provide methods for placing the container downstream to a flow control conduit depositing waste into the container under a positive push force, not a negative vacuum force. Another object of the invention is to provide methods and apparatus in structuration with a draw force including a) enclosing a fluid in a container at fabrication and providing the liquid product in a selectively connectable receptacle, b) disposing the receptacle in a vacuum collection canister system, c) drawing a force along a composite path along a source of waste, d) depositing the waste into a delivery receptacle. Another object of the embodiments herein disclosed is to provide connect ability to a transfer container and a vacuum canister collection lid. Another object of the invention is to provide a composite negative atmosphere draw path formed at least in part by the interior of a transfer container. Another object of the invention is to provide a draw force directed by a composite draw path in part co-acting to transform a delivery container to dispose waste material. Another object of the invention is to provide a canister in structuration with a fluid enclosing supply transfer container forming at least a portion of a composite draw path interposed between a vacuum source and a site of material waste. Another object of the invention is to combine in association with the novel features cited above, a negative draw path force with a material flow path. Another object of the invention is to combine a draw path force with the material draw path to dispose material in a transfer container to remove waste material from a site. Another object of the invention is to provide a throat aperture space/plug/seal disposed in a transfer container access/port site forming at least a part of the draw path controlling draw force towards and away from a transfer container. Another object of the invention is to provide a receptacle derived from a health care fluid delivery sequence converted to co-act with a canister, a lid, a draw force, a composite path, a throat plug to dispose waste. Another aspect of the invention is to to provide supply chain efficiency methods comprising a) fabricating liquid enclosing delivery containers, b) transferring the liquids to a delivery site, c) administering the liquids and connecting the containers in structuration with a waste collection, d) collecting waste. Another aspect of the invention is to provide supply chain efficiency methods comprising a) manufacturing a fluid enclosing container for the distribution of a liquid product b) distributing a liquid product, c) consuming at least a portion of the product d) directing a negative suction vacuum draw force to the container, e) connecting the container to a composite draw path having a suction wand at one end thereof, e) placing the suction wand in suctioning contact with waste material and f) drawing the waste material into the container, g) removing the material in the container, h) disposing the material. Another object of the invention is to a) fabricate a fluid enclosing delivery container for disposal and collection in a waste collection system. Another object of the invention is to a)provide a method of reducing waste comprising enclosing a fluid product in a fabricated delivery container, b) egressing the fluid from the container, c) connecting the container along a vacuum draw path, d) drawing waste material into the container, e) removing the material for disposal, f) disposing the material. Another object of the invention is to provide a method of collecting supplies and transforming them into waste receptacles comprising a) collecting delivery supply containers, b) placing the containers positioned to receive waste in vacuum canisters, c) drawing vacuum, d) controlling the draw force to direct waste material for disposing waste in the transfer container. Another object of the invention is to a) provide a method of converting containers having dispensed at least some container contents, b) converting the container into a vacuum collection system receptive to waste collection and or removal and or disposal. Another object of the aformenetioned objects is to provide a method of handling a dispenser and a receptacle wherein the dispenser is the receptacle. Another object of the invention is to provide a delivery collection container system using fluid enclosing pour bottles fabricated from a blow molding, and/or a continuous blow molding process out of previously shaped polymer performs, and transforming said pour bottles into collection containers. Another object of the invention is to provide a delivery and collection container fabricated from a fluid enclosing blow fill seal manufacturing process container. Another object of the invention is to provide a suction /vacuum system which renders product distribution/transfer containers receptive to waste materials. Another object of the invention is to provide a collection system for reducing waste that is derived from product delivery. Another object of the invention is to reduce internal/external distribution, internal/ external inventory management, whether or not said inventory management is carried out by a vender management program or by a customer. Another object of the invention is for the consumer to account for the cubic volumes of incoming fluids and cubic volumes of outgoing waste materials for analysis and matching incoming and outgoing waste materials to the number of containers needed to optimize the supply purchasing process as practiced within the scope of the instant case.

BRIEF DESCRIPTION OF THE DRAWINGS

FIG. 2 and FIG. 2a comprise an exploded view of FIG. 1.

FIG. 2 shows a top perspective view of a container 14, measuring stand 3 and container 2.

FIG. 2a shows lid 4 and its associated attaching components, handle thrust 6, lock 5, plug 7 spider 8, transfer hose 9, patient hose 11, vacuum hose 10, and cap 15.

FIG. 5a shows dual shot soft seal 4a3 as shown interposed in-between 4o of lid 4 and container flange 14g providing a seal there between.

FIG. 5b shows dual shot soft seal 4f interposed between plug 7 and the inside wall of throat (pour spout) of container 14 providing a seal there between.

FIG. 5c shows dual shot soft seal 4a2 interposed between lid 4 and canister 2 providing a seal there between.

FIG. 6 shows circles around container lid seal and shows a circle lid canister contact area.

FIG. 6a is a blow up of the sealing and contact area between lid 4 and canister rim 2.

FIG. 6b shows a detail of a connection of the connection between thrust 6 and lid 4 as well as the detail of the sealing area between lid 4 and container 14.

FIG. 7 shows a container process whereby container 16 is processed into container 14 which is processed into to container 17 which is processed into container 14. This comprises a disposal chain supply system which relates to FIGS. 19 through 19c on sheet 19 which show various stages of container utility.

FIG. 7a shows potential position of the sealing area between canister 2 and lid 4 defining space 4l having closing seal when thrust 6 is fully oriented clockwise.

FIG. 7b is a blow up detail showing sealing area between container 14 and lid 4 when thrust 6 is in its full clockwise position 6w.

FIG. 8 also shows a blow up detail of the relationship of lid 4 and canister 2 during thrust position 6x.

FIG. 8a shows a gap 41 between canister 2 and lid 4 as thrust 6 takes a counter clockwise orientation 6x.

FIG. 8b shows a detailed blowup of the unsealing relationship of container flange 14g and lid 4 as thrust 6 engages in a counter clockwise orientation 6x.

FIG. 9a shows the unsealing potential at dual shot soft seal 4a2 between canister 2 and lid 4 and depicts space 41 between lid 4 and canister 2 as becoming greater as thrust 6 takes a counter clockwise position 6x.

FIG. 9b shows a blow up detail of the unsealing area between container 14 and lid 4 at 4k. FIG. 9b also shows a blow up detail of the thrust 6 taking counter clockwise position 6x. Thrust thread 6a having lead, height and a pitch contacts container thread 14d. Counterclockwise orientation of 6x creates a thrust motion downward thrusting bottle 14 downward creating a counterforce provided by sealing friction at dual shot soft seal 4a3 and 4a2, said friction imparts a force counter force back through container 14 through thread 14d through thread 6a through thrust 6 which transfer said counterforce through thrust 6 through thrust bottom bearing 6g to bearing surface 4a9 of lid 4. This action counter action (effect cause effect) comprises an easy way for the separation of bottle 14 and lid 4 at sealing area 4k as well as canister 2 an lid 4 at sealing area gap 41. Thrust 6 provides an easy to rotate smooth significant force giving a mechanical disassembly for the sealing and unsealing of a container lid and bottle.

FIG. 10a is a blow up detail jacking lever 21 flexed into a downward jacking position providing seal separation between canister 2 and lid 4.

FIG. 10b shows thrust 6 in an intermediate orientation between 6x and 6w defining a counter clockwise effect causing an effect of unsealing container 14 and lid 4 at 4k.

FIG. 11a shows the acting of jack lever keel 21b having contacted canister 2 at 2b after lever jack 21 has been flexed downward providing a mechanical leverage for the separation of lid 4 and canister 2.

FIG. 11b is a blow up detail of thrust 6x at an intermediate counterclockwise orientation 6x of FIG. 10b further defining a process of thrust effect and counter effect describing the vertical thrust forces moving the container 14 down relative to lid 4 and unsealing the lid and bottle at 4k.

FIG. 14a shows a blow up detail of the leverage jack making contact with container 2.

FIG. 14b sows thrust bearing 6 in a full clockwise orientation.

FIG. 15a shows a cross section of lid 4 taken at one of two perpendicular sections that would show one of four locks 5 in an up unlocked position and one of four locks 5 locked in a downward locked position.

FIG. 15b shows a blow up detail of lock 5 up in the unlocked position and spring lock 4r in its unlocked/unengaged resting position.

FIG. 15c shows one of four locks 5 in a downward locked position showing lock push ramp 5c having moved the end of spring lock 4r into an interference locked position under canister lip 2f.

FIG. 17a is a blow up detail of lock 5.

FIG. 17b is a blow up detail of thrust bearing 6.

FIG. 17c is a blow up detail of thrust bearing retaining hook 4f of lid 4 and thrust handle surface 4a9 if lid 4.

FIG. 17d is a blow up detail of jacking lever 21.

FIG. 18a shows a side elevation view of a container depicting its height and a dimension showing its thread.

FIG. 18b shows another container size depicting its height and depicting a dimensions from its top to the sealing area.

FIG. 18c shows a side elevation view of an alternative bottle size showing a dimension of its height and a dimension of its center to its flat side wall.

FIG. 18d is a side elevation cross section of the assembly of canister 2 and measuring stand 3 showing a dimension of the bottom of said stand, to the bottom of stand bottle slot showing a dimension of subassembly center line to inside wall of said bottle slot and showing a dimension of sealing rim canister 2 and a bottle thread height as further depicted in FIGS. 18e, 18f, and 18g.

FIG. 18e shows a side elevation view showing measuring stand 3 in two parts, 3a and 3b. A large container, a dimension between the bottom of stand 3 and the bottom of bottle slot a dimension showing the center of the sub assembly and the inside of bottle support stand and a dimension showing the top of the bottle to the bottle flange seal 14g.

FIG. 18f is similar to the FIG. 18e but showing an alternative container size.

FIG. 18g is similar to FIGS. 18e and 18f showing an alternative container size. It is important to note that thread height 14j of FIG. 18a dimension 14q of FIG. 18b dimension 14o of FIG. 18c dimensions 14t of FIG. 18d, e f, & g, and dimension 3u of FIGS. 18e, f, & g as well as dimensionl4s of FIGS. 18a, b, & c all correspond to matching a thread having a thread height, a thread having a thread pitch, a thread having a thrust lead to thrust handle such as 6 shown in FIG. 16 and other figures of the instant case such that a single thread or a common thread of an extremely high volume containers made in various volumetric cubic capacities, such as 14, 14a, 14b, 14c, etc., may all be functionally co-apted into a collection system designed for supply chain efficiency such that XX-nut dimension and XX-bottle of FIG. 15 as well as the assembly contact points of z, x, and the alignment assemblies aided by leads 4g, 4h, 3w, 14v, 14g, all provide horizontal and vertical alignment system that is easy to assemble such that thrust thread 6a and bottle thread 14d properly engage without undo attention.

FIG. 19a depicts a container which has been hermetically sealed enclosing some sterile/other liquid 16b.

FIG. 19b shows an empty container in sequence waiting to be placed into the canister system of the preferred embodiment (the apparatus of FIG. 19 with its cap having just been removed.

FIG. 19c shows lid 4 removed from the subassembly of the preferred embodiment.

DETAILED DESCRIPTION OF THE DRAWINGS

Figure 1:
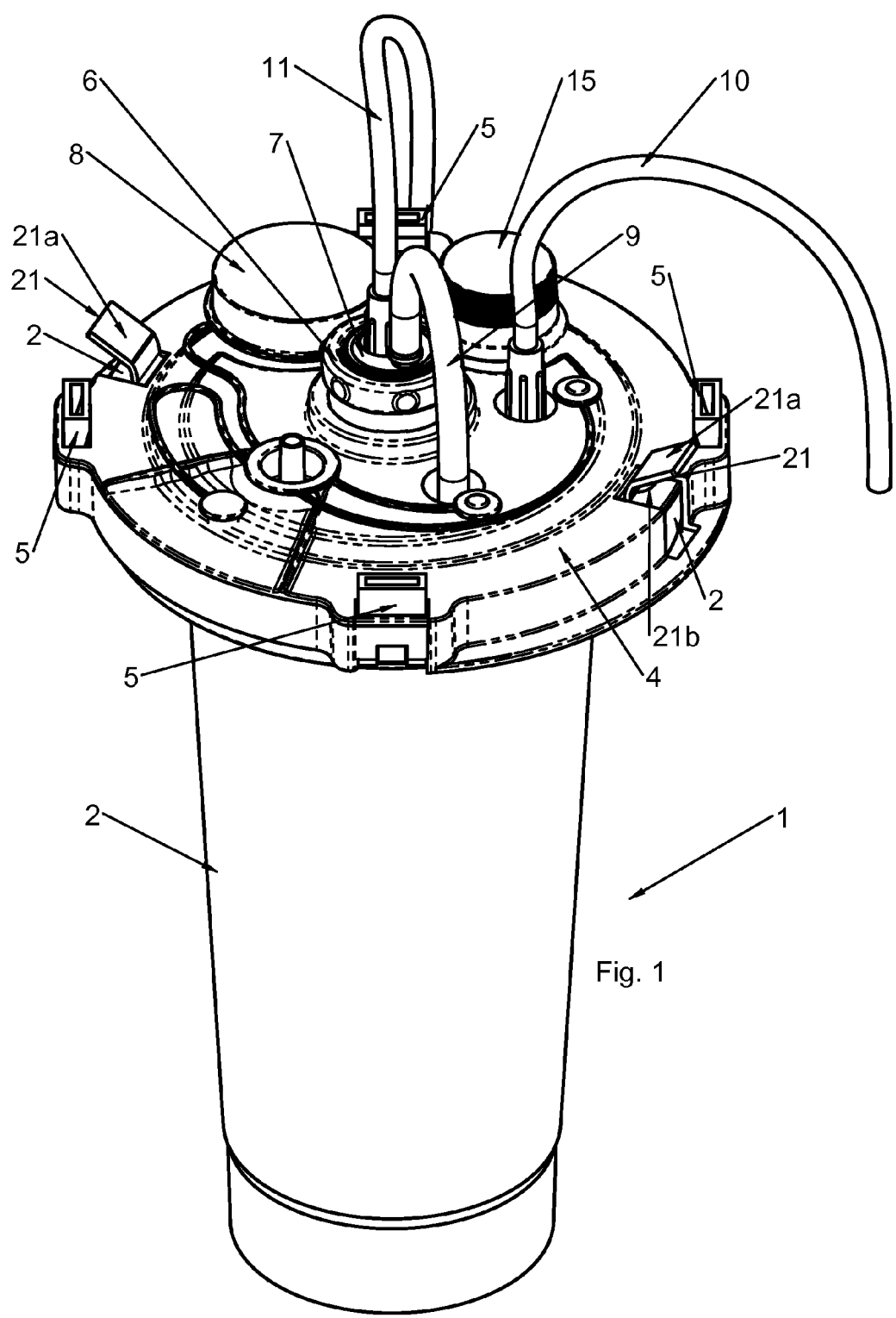
FIG. 1 is a top perspective view of a disposal chain supply system.

FIG. 1 is a top perspective view showing the system of the preferred embodiment 1, canister body 2, lid 4, four locks 5, thrust handle 6, plug 7, spider cap 8, transfer hose 9, vacuum transfer hose 10, patient hose 11, leveraging jack 21, and pressure surface 21a of leveraging jack 21.

Figure 2:
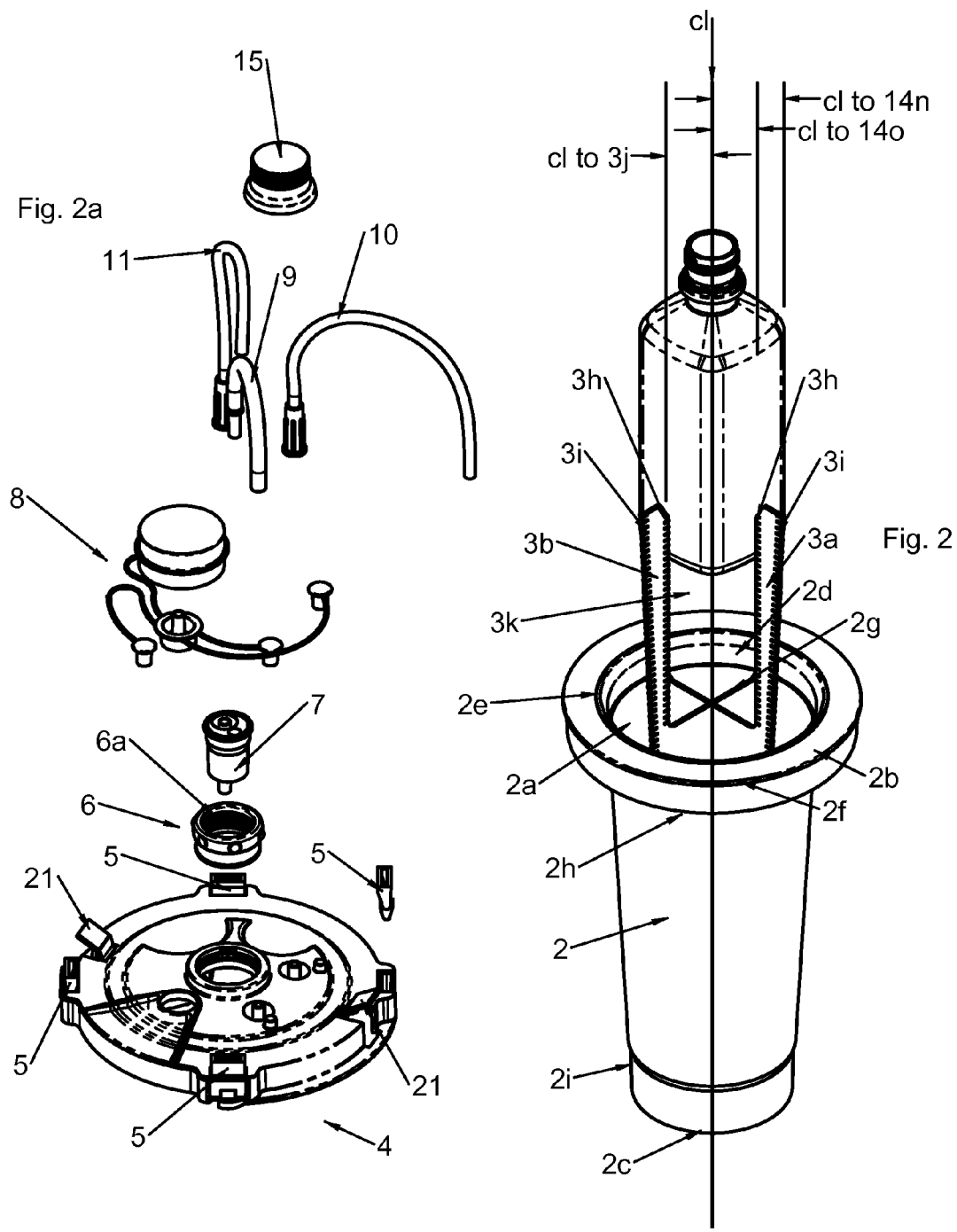

FIGS. 2 and 2a is an exploded view of the system in two parts. Referring to FIG. 2 specifically, showing a centerline of the exploded assembly vertically up and down the center of the parts. Canister body two is shown with base 2c, stack rim 2l, interference lip 2f, contact surface 2b, main housing body 2, carrying rim 2h, inner housing space 2a, horizontal top surface seal 2e, and angled inner surface seal 2d. Also shown is measuring stand 3, featuring cutout card 3a and cutout card 3b, one of which is manufactured with a slot so the two cards may be assembled perpendicular to each other so that they nest into inside of canister 2. Measuring indicia 3h is shown which has incremental volume measurement markings relative to fluid collecting into container 14 and incremental volume measurement markings 31 relative to fluid collecting which may be collected in an overflow from container 14 and into canister 2. It is important to note the inside distance from centerline to 3j, the inside edge of the measurement stand post as well as to the measuring distance from the centerline from 14n the corner of container 14.

Referring to FIG. 2a showing cap 15 of container 14, patient hose 11, vacuum transfer hose 9, vacuum source hose 10, spider cap 8, plug 7, handle thrust 6 having inside thread 6a, one of four locks 5, an jacking lever 21.

Figure 3:
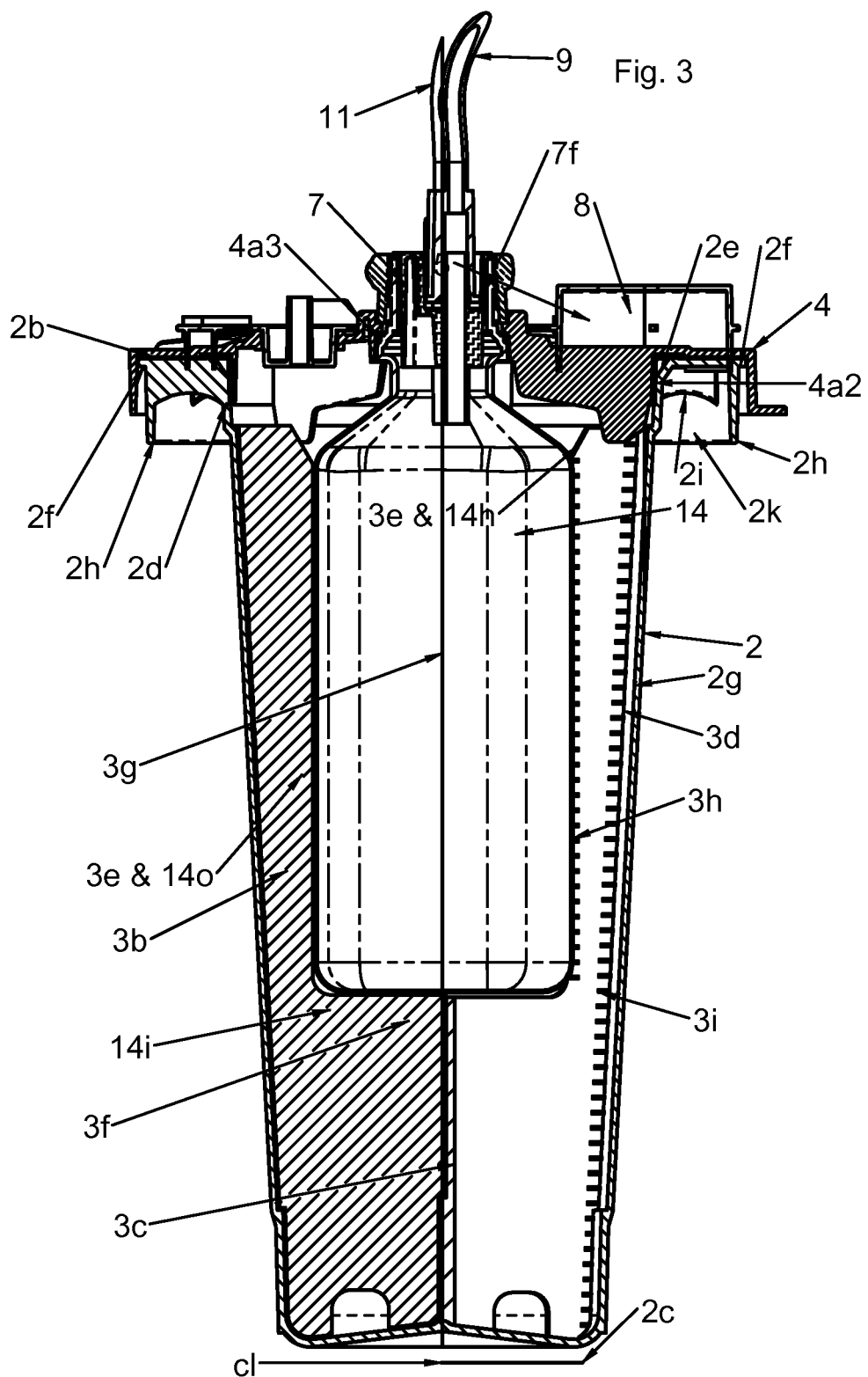
FIG. 3 is a cross section of the embodiment shown in FIG. 3 showing 3 blow up circles to illustrate the location of dual shot soft seals. The Embodiment of FIG. 4 has a break at an intermediate portion along the canister and measurement stand.

FIG. 3 shows a cross section of component parts in their assembled position. Shown is patient hose 11, vacuum hose transfer hose 9, plug 7, dual shot plug soft seal 7f, spider cap 8, dual shot soft seal 4a3, dual shot soft seal 4a2, canister lock interference lip 2f, lock 5, contact surface 2b of canister 2, canister carrying rim 2h, canister rim support struts 2i, canister finger curl space 2k. Container 14 sealed to lid 4 by threadable engagement using handle thrust 6. Measurement card 3a and 3b are seen nested with canister 2 and are supporting container 14. Canister 2 sits on its stable base at 2c.

Figure 4:
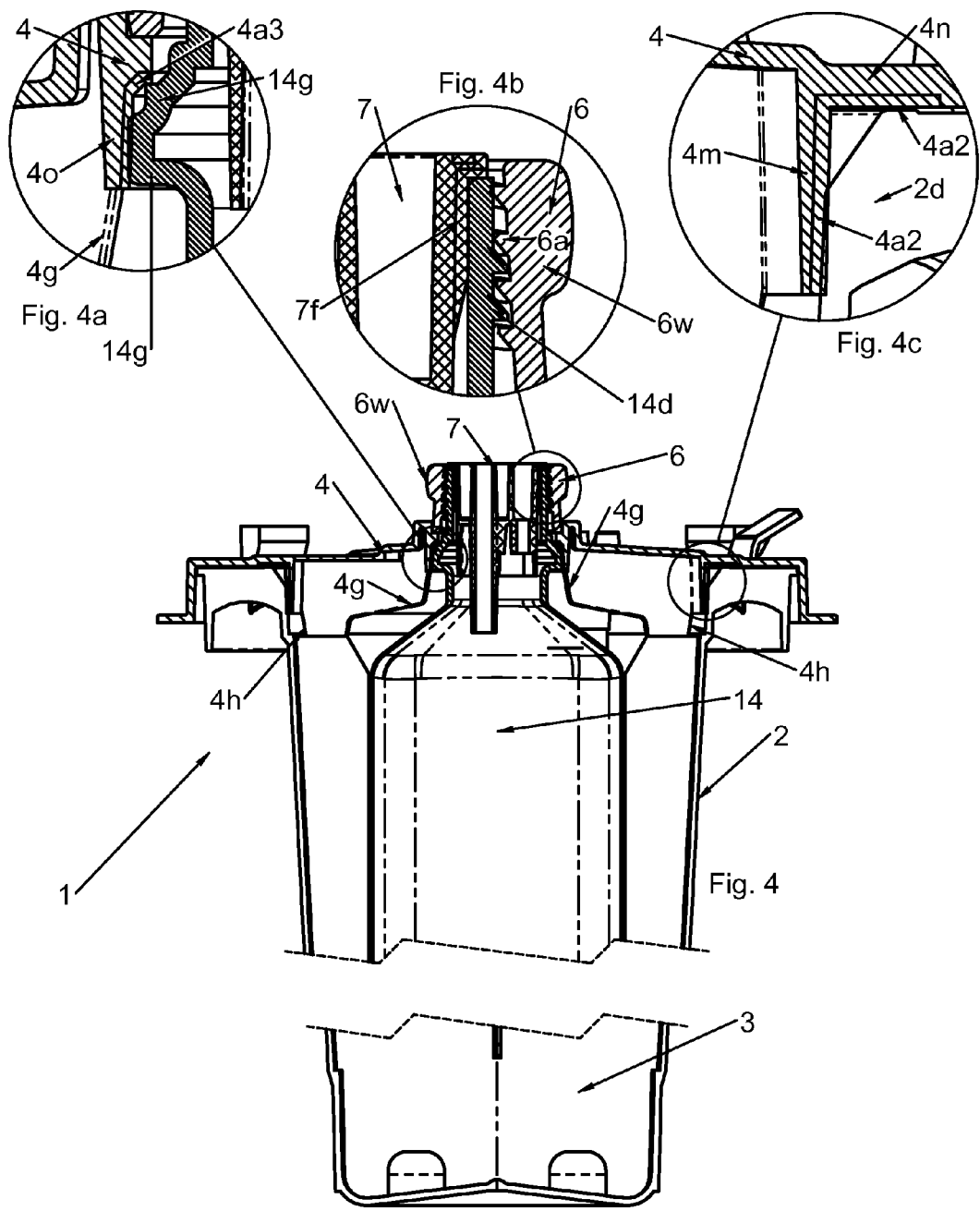
FIG. 4a shows a blow up of a dual shot soft seal 4a3 attached to lid 4 at 4o during molding of lid 4.
FIG. 4b shows dual shot soft seal 7f attached to plug 7 as it is affixed to plug 7 during molding of plug 7.
FIG. 4c shows dual shot soft seal 4a2 attached to lid 4 along surface shown at 4n and surface 4m.

FIG. 4 shows a cross section of system 1 with canister 2 measuring stand, cards 3a and 3b and bottle 14 cutaways. Lid 4 shows assembly bevel leads 4h and 4g which are associated with a plurality of strut support wall sections extending downwardly from the main level of lid 4. Bottle 14 is thread ably engaged handle thrust 6 with handle thrust 6 fully clockwise oriented 6w in a fully sealable position.

FIG. 4a is a blow up showing the seal between bottle 14 and lid 4. Bottle flange 14g engages dual shot 4a3 of lid 4. Dual shot 4a3 is molded into lid 4 at 4o.

FIG. 4b is a close up detail showing the dual shot seal interposed between plug 7 and the throat of canister 14. Also shown is bottle thread 14d engaged with handle thrust thread 6a. Handle thrust 6 is shown in a full clockwise orientation 6w. This view also depicts showing a cross section of interposing a soft dual shot seal between plug 7 and bottle neck 14 peripherally. This view also depicts showing interposing the neck of bottle 14 between a plug 7 and a handle thrust 6.

FIG. 4c shows a blow up of a cross section showing the interposing a soft dual shot 4a3 between lid 4 and canister 2. Dual shot 4a2 is molded into lid 4 during molding of lid 4 and provides a seal horizontally at 4n and substantially angularly at 4m of lid 4.

Figure 5:
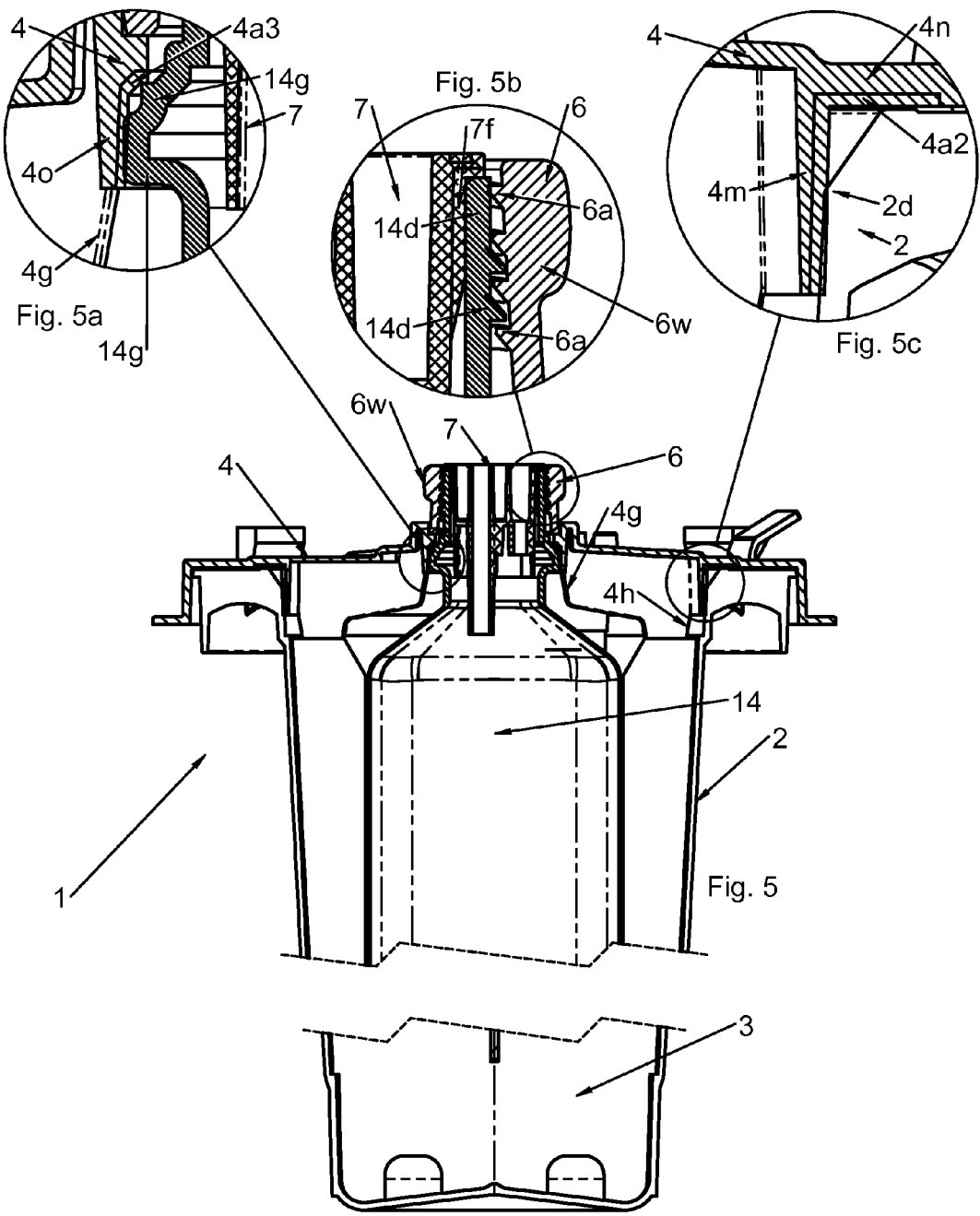
FIG. 5 show a cross section of embodiment show in FIG. 4 depicting the relationship of the three seals described in FIGS. 4, 4a, 4b and 4c. When thrust 6 is rotated clockwise to its endpoint the three said seals and associated mating and sealing surfaces and components are shown sealed in the above three blow up figures.

FIG. 5 is a cross section of system 1, showing measurement stand 3, canister 2, bottle 14, lead bevel 4h of lid 4, lead bevel 4g of lid 4, lid 4, plug 7 handle thrust 6 and 6w depicting the handle thrust 6 fully orientated clockwise fully forming a seal between bottle 14 an lid 4.

FIG. 5a shows a blow up detail of dual shot 4a3 as handle thrust 6. FIG. 5 is rotated clockwise as bottle flange 14g is increasing engages lid at 4o notably as a result of slight draft angle lead 4o.

FIG. 5b show plug 7 soft dual shot seal 7f, bottle thread 14d, handle thrust thread 6a all being respectfully oriented in full counterclockwise orientation.

FIG. 5c shows a blow up detail of soft dual shot 4a2 interposed between lid 4 and canister 2 at horizontal 4n and substantially vertically angled surface 4m of lid 4.

Figure 6:
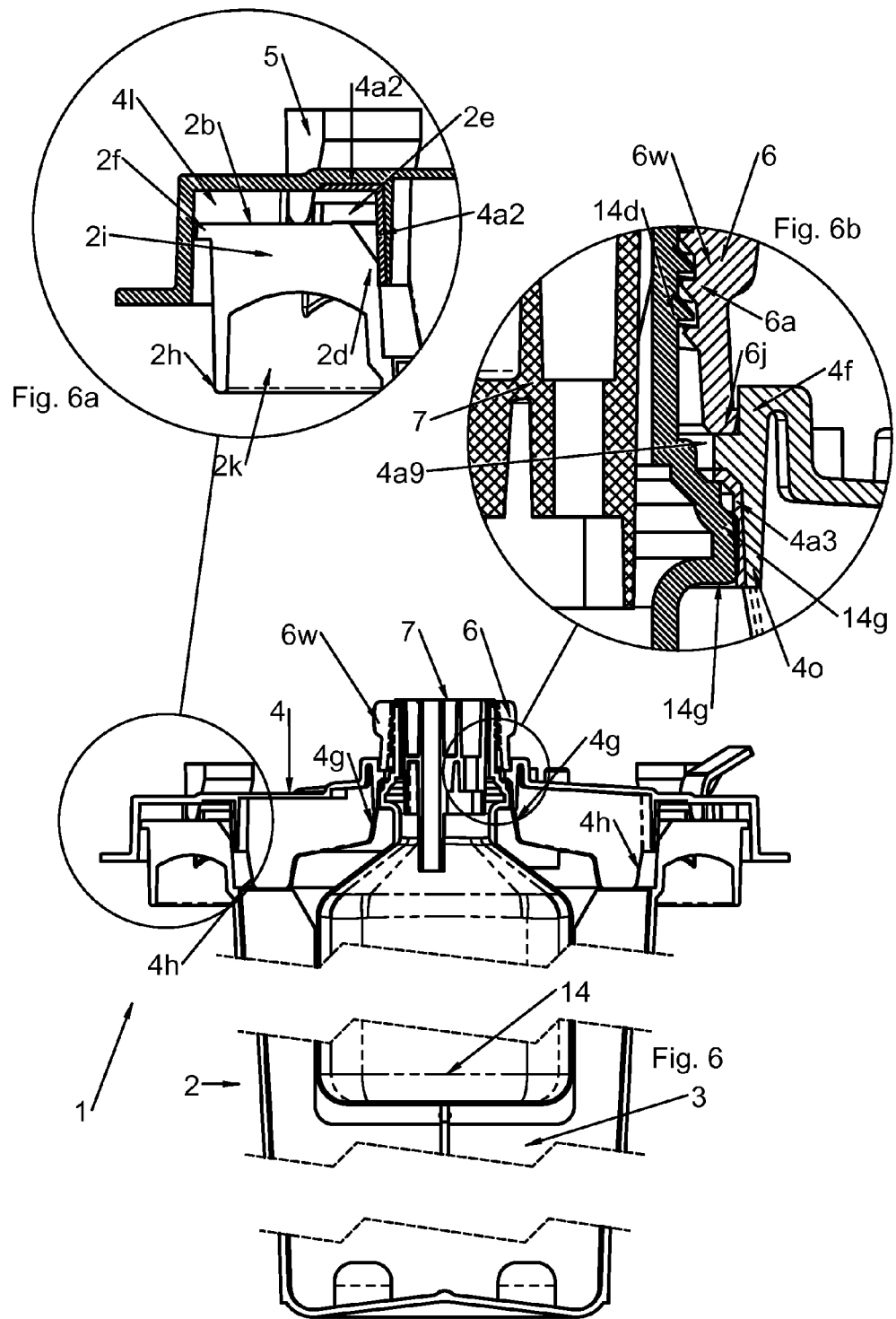
FIG. 6 is a cross section as shown in FIGS. 4 & 5 showing two breaks along the area of canister body 2.

FIG. 6 shows a cross section of FIG. 1 having 2 breaks along the vertical rise of canister 2, bottle 14, measurement stand 3 as well as a lower break across canister 2 and measurement stand 3. This view shows lid 4 having two lead bevels 4g and 4h, handle thrust 6, plug 7 and 6w depicting handle thrust 6 in a fully clockwise bottle/lid sealing orientation.

FIG. 6a is a blow up showing finger curl lifting/carrying space 2k of canister 2, lower canister rim 2h, rim strut supports 2i, substantially vertically angles canister seal surface 2d, substantially horizontal canister seal surface 2a, soft dual shot seal 4a2, horizontal and vertical 4a2, lock 5 in an up unlocked position, contact surface 2b of canister 2, separability space 4l showing separation between canister 2 and lid 4, and interference lock lip 2f of canister 2.

FIG. 6b shows a blow up detail depicting bottle flange 14g plug 7, soft dual shot bottle/lid seal 4a3 thrust handle bearing portinsurface 4a9, thrust handle retaining hook 4f of lid 4, thrust handle hook 6j, thrust handle thread 6a, thrust handle 6, and 6w depicting the thrust handle in full clockwise sealing orientation.

Figure 7:
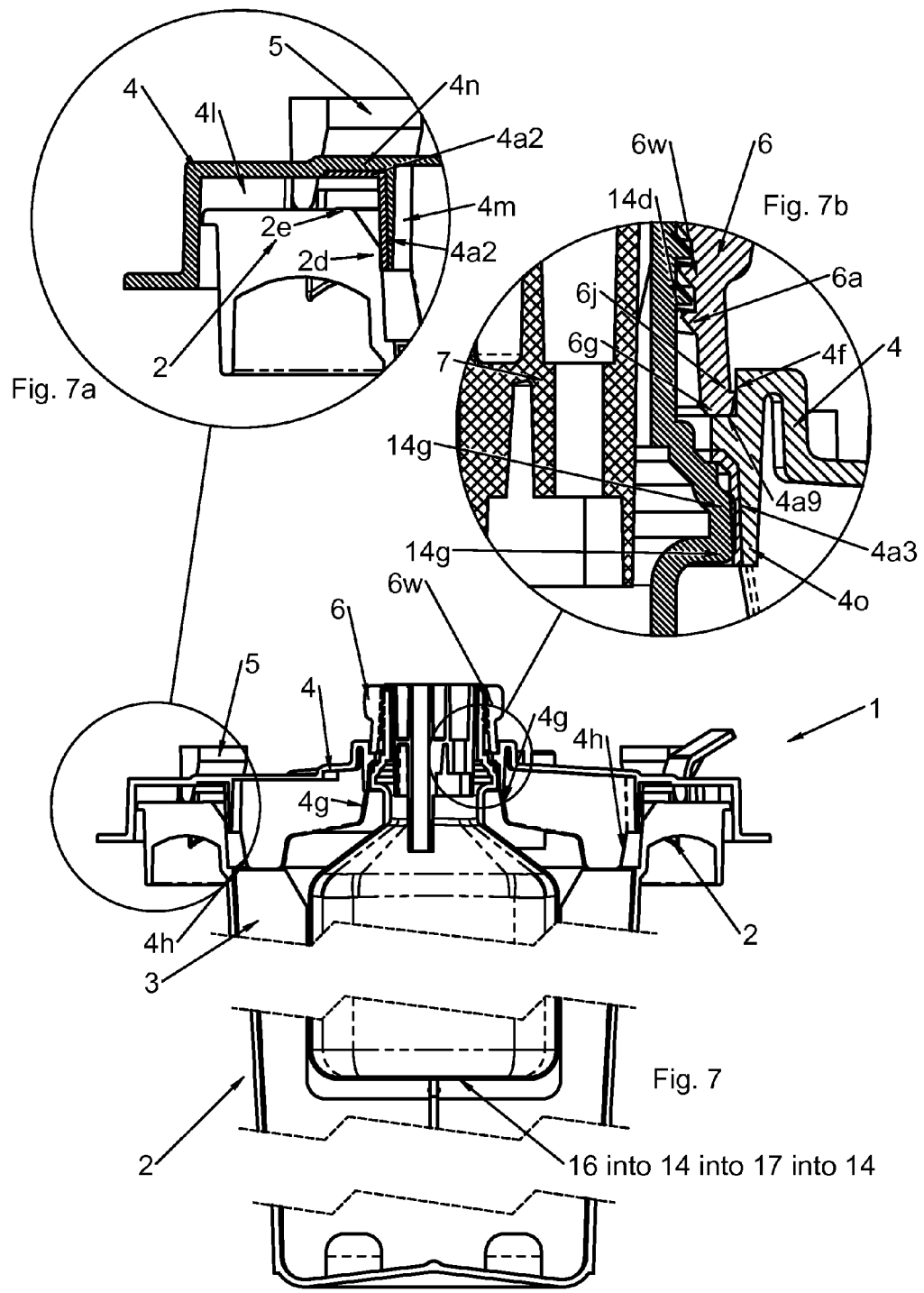
FIG. 7 is a cross section of the embodiments of FIGS. 4, 5 & 6 showing two breaks along the canister body and having circles around the container lid sealing area and the lid canister sealing area.

FIG. 7 depicts a cross section of system 1 depicting canister 2 and stand section card 3. This shows two breaks along the vertical rise of canister 2, card measurement stand 3, bottle 14 as well as a lower break across canister 2 and measurement stand 3. This view shows canister assembly bevel lead 4h and bottle assembly bevel lead 4g, one of four locks 5, lid 4, thrust handle 6.

FIG. 7a is a blow up detail defining separability space 4l defining separation between canisters 2 an lid 4. Horizontal canister sealing surface 2e and substantially vertical canister sealing surface 2d, dual shot soft seal 4a2, substantially horizontal and vertical dual shot soft seal 4a2, at 4n and 4m of lid 4 and one of four locks 5 show up in unlocked orientation.

FIG. 7b depicts handle thrust 6 in its full clockwise sealing orientation as depicted by 6w showing the engagement of bottle thread 14d and handle thrust thread 6a. As handle thrust 6 takes its clockwise sealing orientation as thrust bottom 6g contacts handle thrust bearing surface at 4a9 to the extent a light amount of friction resistance occurs as bottle flange 14g moves upwardly along soft dual shot seal 4a3 which is interposed between lid 4 and at 4o and bottle flange 14g.

Figure 8:
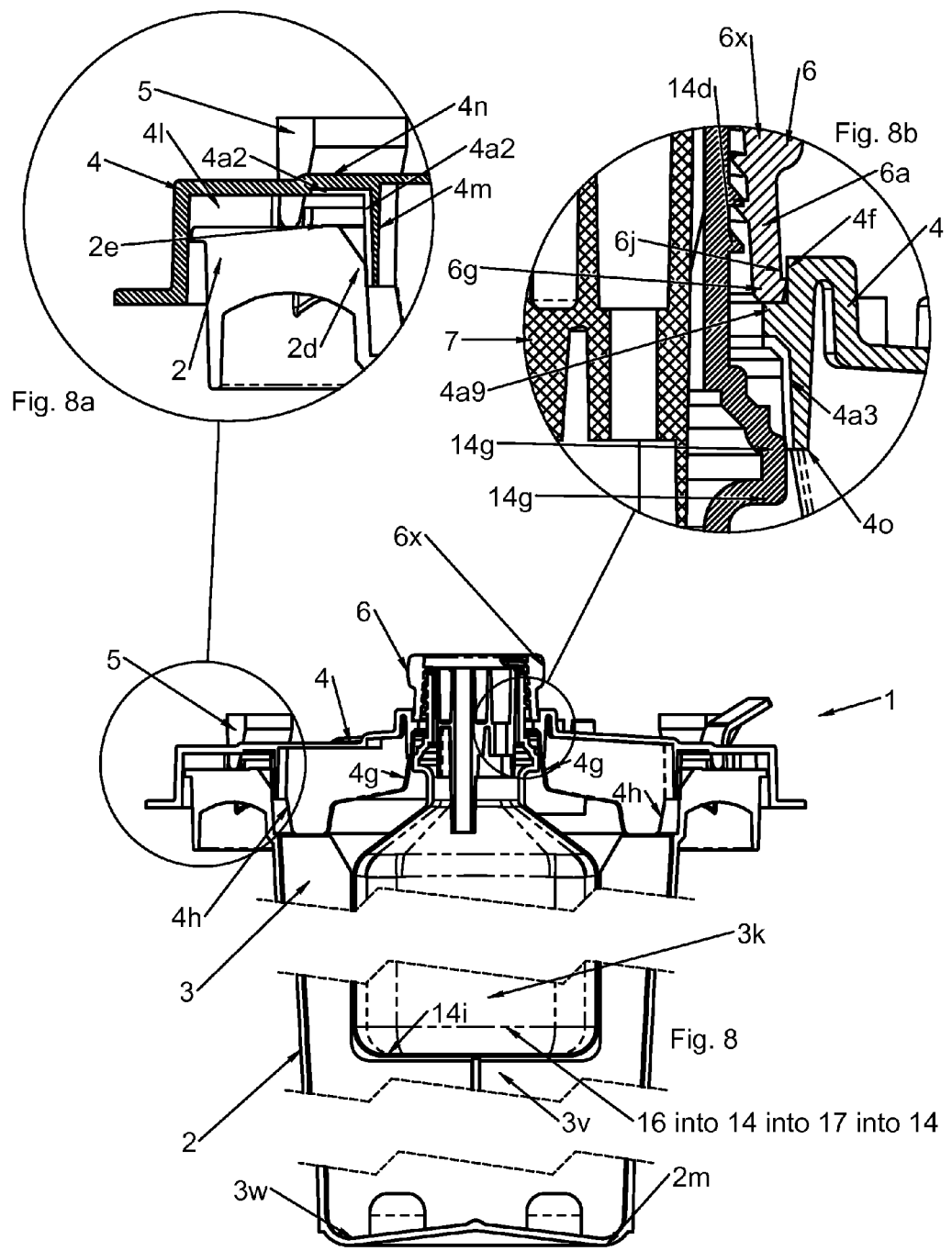
FIG. 8 is a cross section of the preferred embodiment showing detailed blow up circles of thrust 6x as it may be engaged in counter clockwise unsealing orientation.

FIG. 8 is a cross section view of the preferred embodiment 1 having two breaks along the vertical rise of canister 2 and measurement stand 3, and also across bottle 14. Indicia on this sheet shows a utility cycle of disposal chain supply systems container and fluid management as it relates to sheet 19 of 23. 16, depicting a hermetically sealed bottle, which becomes empty into bottle 14, which becomes inserted into a canister system which becomes a supply bottle having surgical suction waste, disposed therein which becomes 14, another empty bottle after fluid disposal. Also shown is canister bottom 2m, measurement stand bottom 3w, canister 2, bottle slot bottom 3b, bottle bottom 14i, assembly canister lead 14h, assembly canister lead 4h, and bottle canister lead 4g, one of four locks 5, in an unlocked position, lid 4, handle thrust 6, and 6x depicting handle thrust having been rotated clockwise in a unsealing orientation.

FIG. 8a is a blow up detail of the effects of handle thrust orientation 6x in that separability space 4l is enlarged by counterclockwise unsealing orientation of handle thrust 6, also depicted is canister 2, canister sealing surface 2d and 2a associated with horizontally and substantially vertically angled soft duals hot seal 4a2 of lid 4 at 4n and 4m.

FIG. 8b is a close up detail of the bottle lid and sealing orientation, 6x of handle thrust 6 during counterclockwise unsealing orientation 6x of thrust 6, container thread 14d is engaged by handle thrust 6a initiating a downward motion on container 14 effecting contact of thrust rim 6j upon lid hook 4f of lid 4, similarly causing container flange 14g to move downwardly unsealing from soft dual shot 4a3 and unseal ably engaging 4o of lid 4.

Figure 9:
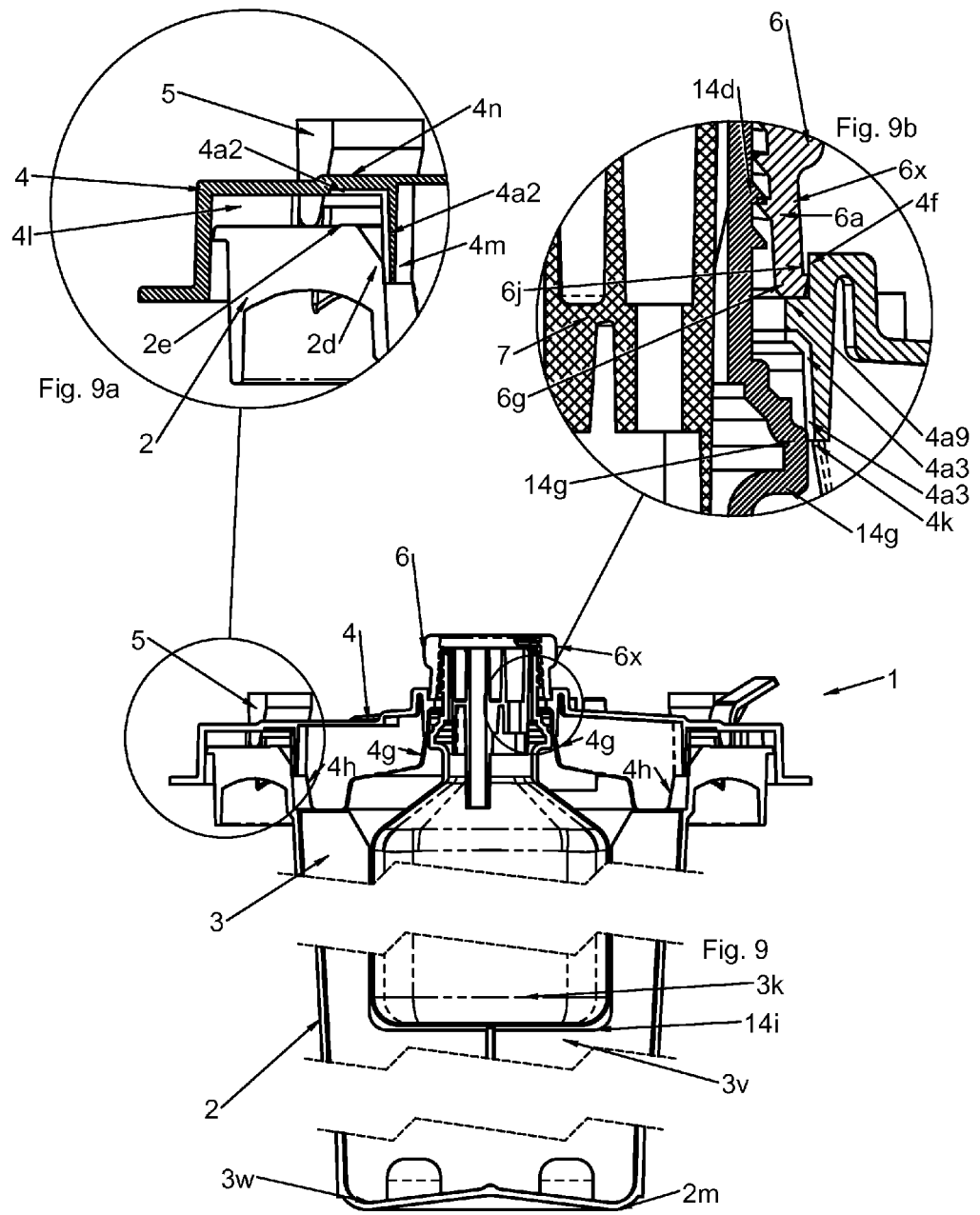
FIG. 9 shows a cross section of the preferred embodiment having two breaks along the canister body.

FIG. 9 is a cross sectional view of the preferred embodiment 1 showing canister base 2m, measurement stand base 3w, measurement stand bottle slot bottom 3b canister 2 measurement stand 3, bottle bottom 14i handle thrust 6 in counterclockwise unsealing orientation 6x. Also shown is lid 4, and lock 5 in and upward unlocked position.

FIG. 9a is a respectively the same figures as shown in FIG. 8a. Shown in FIG. 9a is container flange 14g, unsealing from sealing space 4k, disengaging duals shot soft seal 4a3. As handle thrust 6 is moved counterclockwise unsealing orientation 6x further producing and upward force, 65j continuing as bottle flange 14g drops below sealing space 4k. As bottle thread 14d continues to engage handle thrust thread 6a even thought bottle sealing flange 14g is completely disengaged with soft dual shot seal 4a3, handle thrust 6 continues its counterclockwise orientation of unsealing. We must refer back to FIG. 9 which shows a further downward motion of container 14 enacting contact force between bottle bottom 14i and measurement stand sot bottom 3b, further enacting force between measurement stand bottom 3m and canister at 2m continually moving the bottle down further enacting an unsealing force increasing separability space 4l and unsealing lid from canister 2 at dual shot seal 4a2, as the counterclockwise handle thrust 6 xs continually unseals the bottle 14 and the lid 4 and the lid 4 form canister 2.

Figure 10:
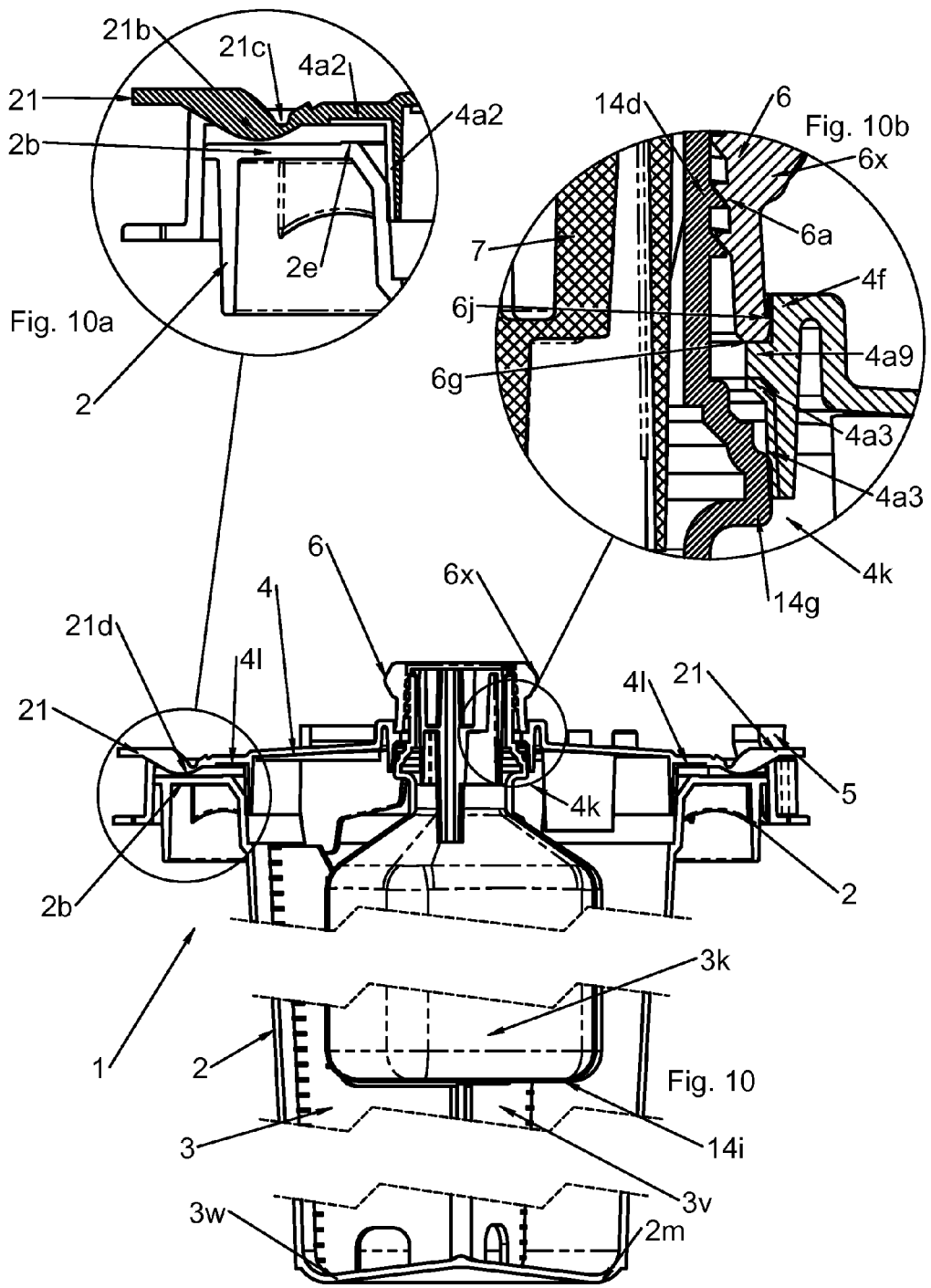
FIG. 10 shows the preferred embodiment showing circles of detail blow up thrust 6x in a thrust position intermediate to that as shown in the Figures on sheet 4 and sheet 5 and sheet 6 and sheet 7 and sheet 12 of the dimensions with respect to the thrust position shown in sheets 8 and sheets 9.

FIG. 10 shows substantially similar cross section views as shown in FIGS. 6, 7, 8, and 9, however handle thrust 6 is taken and intermediate unsealing/sealing orientation as well as jacking lever 21 is shown flexed down whereby push off keel 21b of jacking lever 21 makes contact with canister contact surface 2b further increasing separability space 4l.

FIG. 10a is a blow up detail of jacking lever 21 having been flexed at flexion detent 21c such that push off contact keel 12b makes contact with canister 2 at contact surface 2b causing further separation between lid 4 and canister 2 at dual shot soft seal 4a2.

FIG. 10b depicts handle thrust 6 in an intermediate counter clockwise unsealing orientation depicting container flange 14g in a partial disengaged and unsealed orientation with respect to dual shot soft seal 4a3 at sealing space 4k, and during unsealing, counterclockwise orientation 6x of thrust lever 6 enacts unsealing friction at sealing area 4k between container flange 14g and dual shot soft seal 4a3 which creates a counter upward force effect back through bottle neck 14d, engaging thread 6a, such that handle thrust hook rim 6j exerts an upward producing motion and force on lid retaining hook 4f of lid 4.

Figure 11:
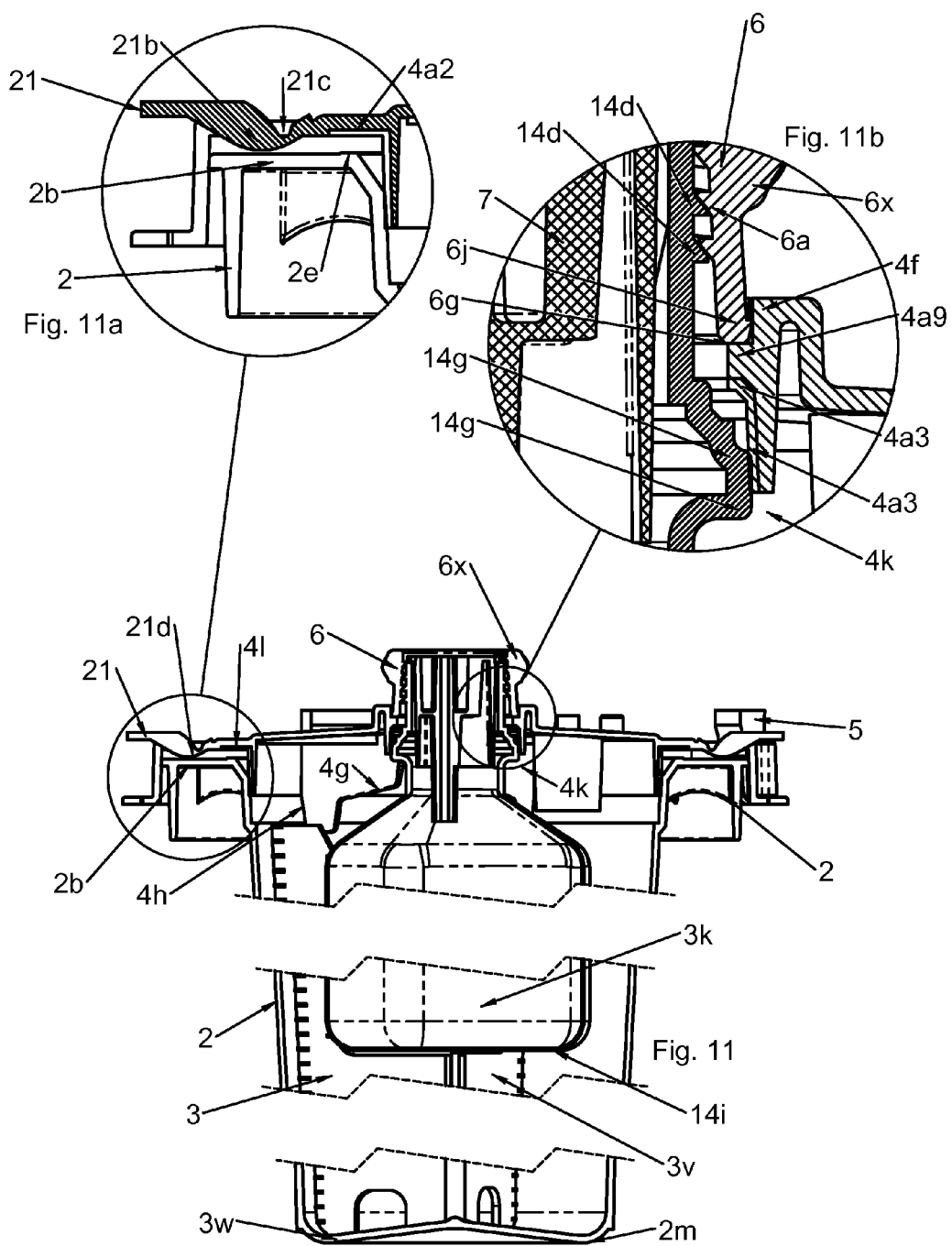
FIG. 11 shows the preferred embodiment of FIG. 10.

FIG. 11 shows a substantially similar cross section of the preferred embodiment as shown in FIG. 10.

FIG. 11a shows substantially similarly positioned leverage jack 21 having been flexed downward at 21c allowing push off contact keel 21b to make contact with canister contact surface 2b. Also shown is lift rim 4a and in this scenario, the operator would place a thumb on jacking leverage 21 and place the fingers underneath finger lift rim 4u of canister lid 4 in opposing digital fashion allowing the facilitation of separation of lid 4 and canister 2.

Figure 20:
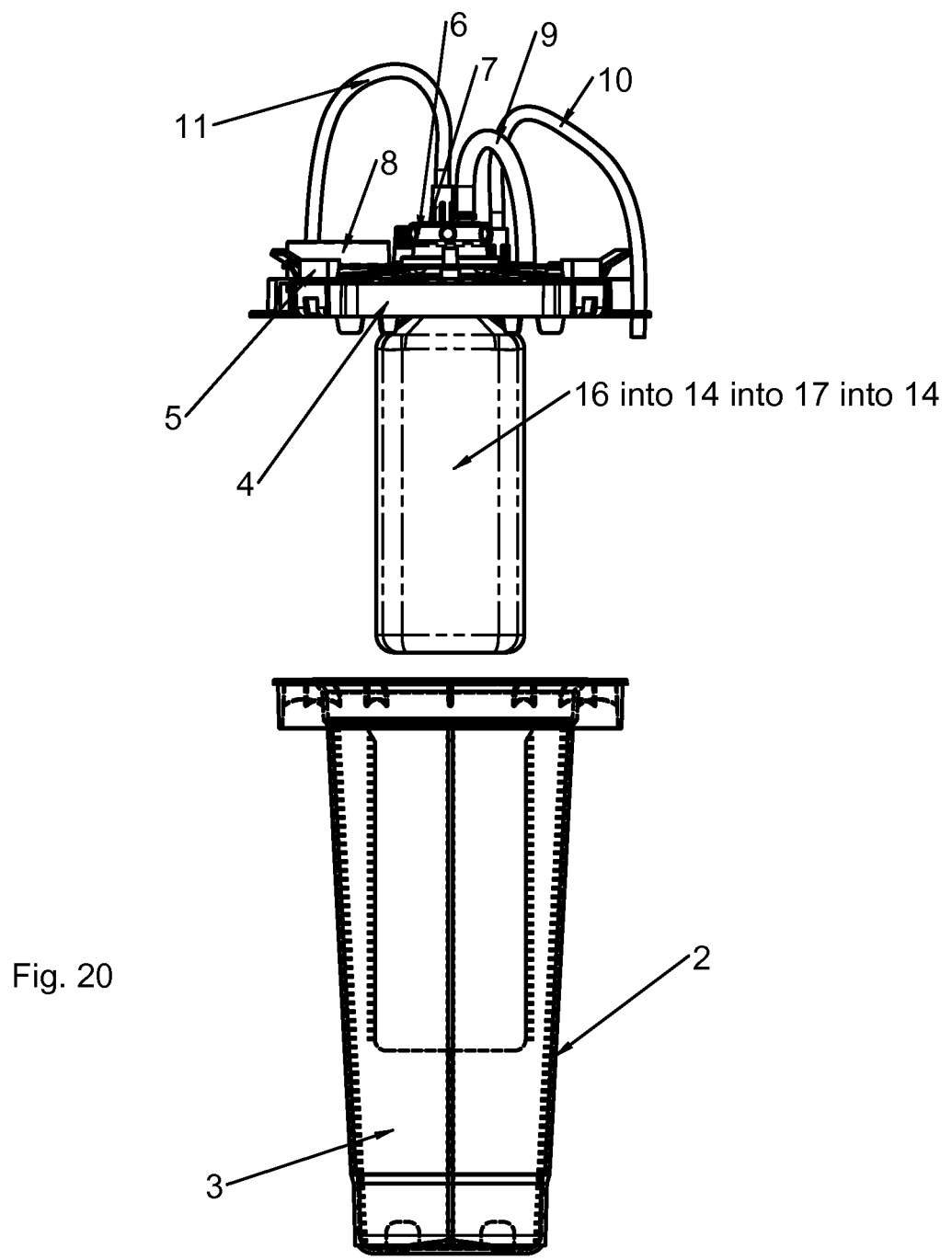
FIG. 20 shows an alternative means of separating the container's lid 4 subassembly from canister 2 and measuring stand 3.

FIG. 11b shows the relationship between the bottle 14 and lid 4 in similar handle thrust orientation 6x as shown in FIG. 10b. This figure depicts the positional disassembly option of the system which is that the leverage jack 21 may be pushed down so that contact keel 21b will push off canister 2 at 2b creating an upwardly jacking motion while finger lift rim 4u provides a lifting surface for opposing finger action for the disassembly between lid 4 assembly and canister 2. As illustrated in FIG. 20 of sheet 23.

Figure 12:
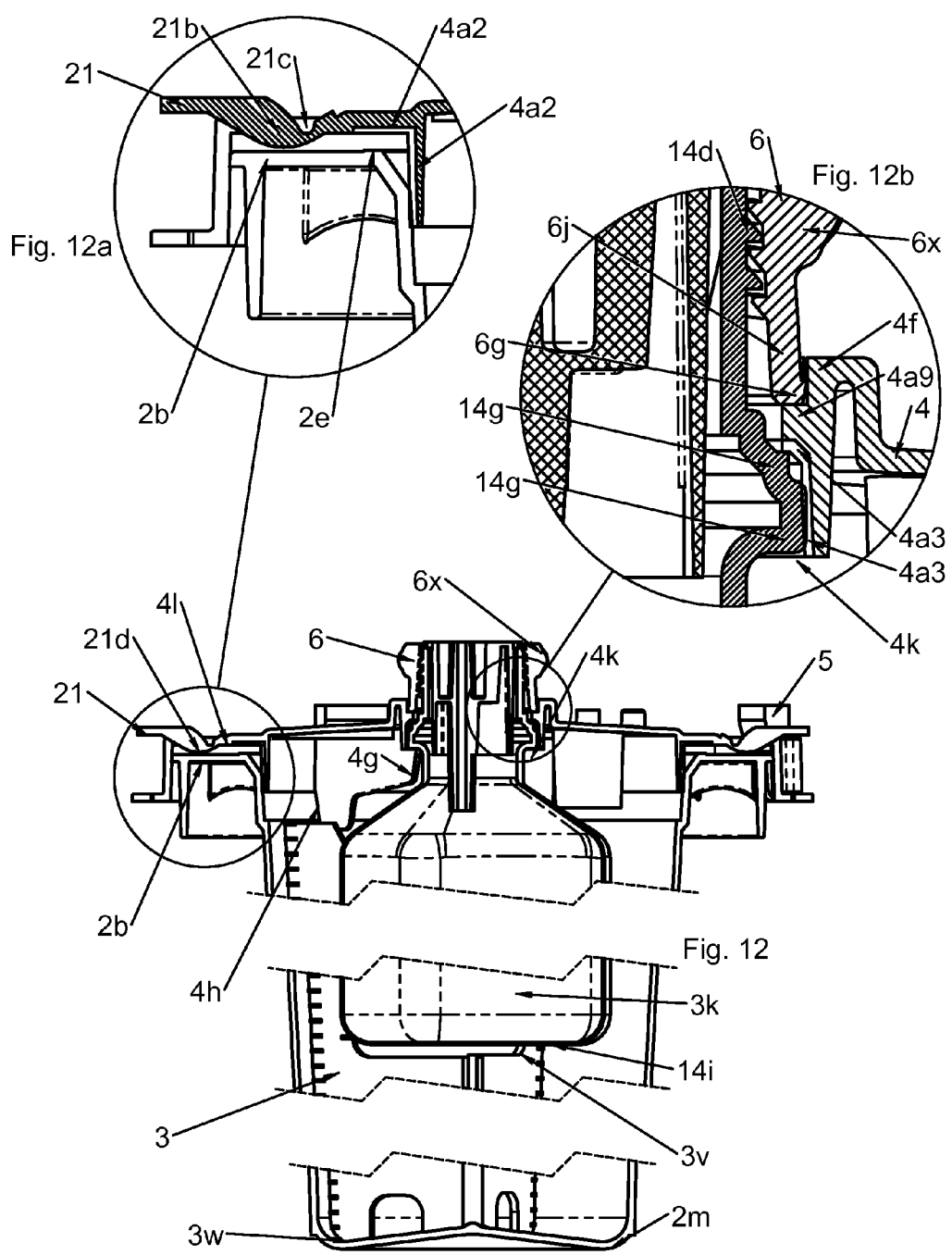
FIG. 12 is a cross section of the preferred embodiment defining blow ups of seal area 4k and jacking lever 21.

FIG. 12 shows a similarly oriented cross section of the preferred embodiment showing bottle 14 and lid 4 in full sealing orientation by the full clockwise orientation of 6x of handle thrust 6 and is noted here that a slight gap exists between container bottom 14i and measurement stand slot bottom 3v. This gap may also be achieved by downward thumb pressure on jacking lever 21 and upward finger lifting of finger rim lift 4u.

FIG. 12a shows similar orientation of jack lever 21 making contact with contact surface 2b canister 2, by push off contact keel 21b.

FIG. 21b shows substantially the same blow up detail as that of FIG. 7b.

Figure 13:
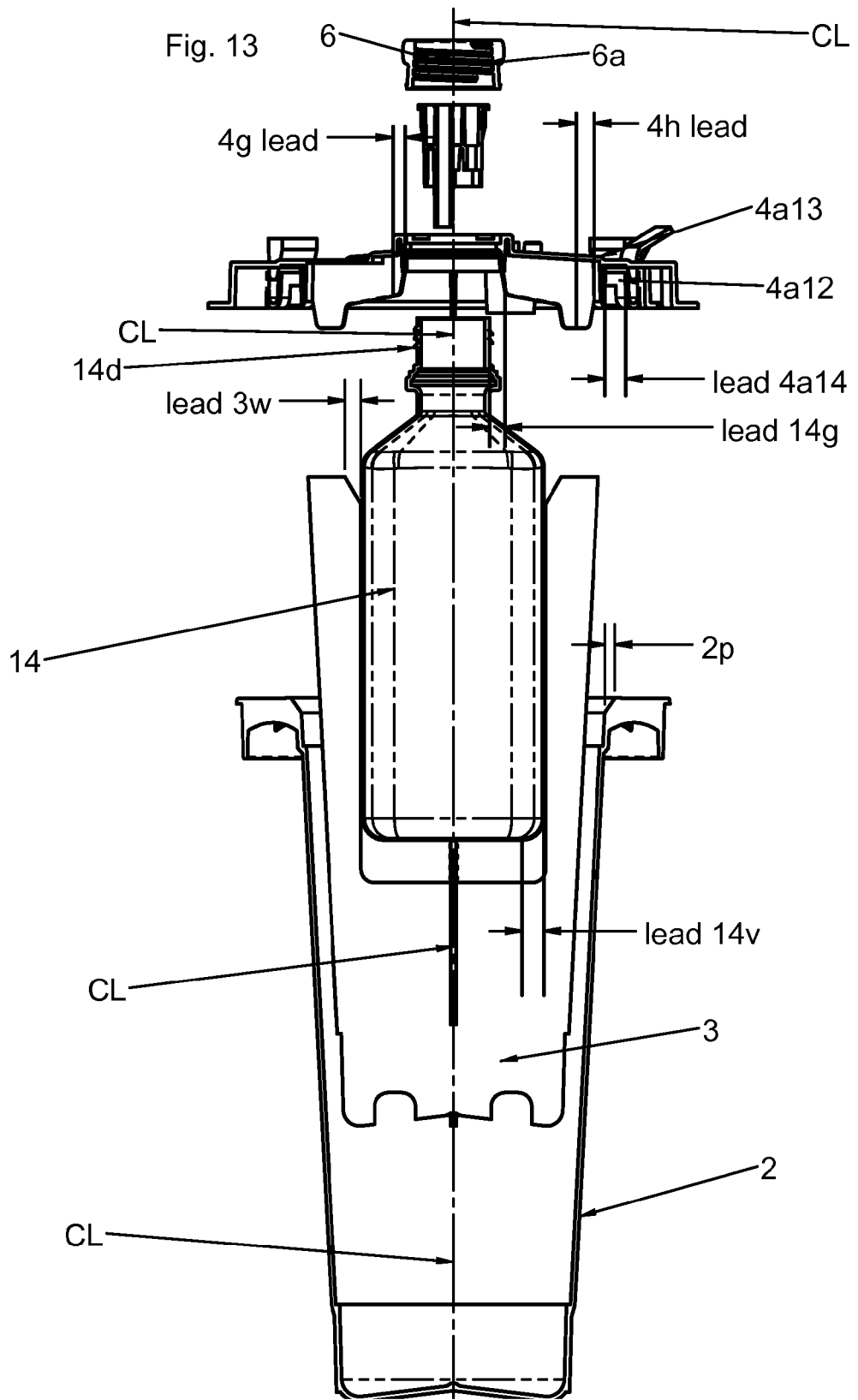
FIG. 13 shows an exploded view of canister 2 measuring stand 3, container 14, lid 4, plug 7 and thrust handle 6 with respect to an alignment relationship with a centerline as shown. Also shown are various component bevel/leads which are illustrated to show simpler assembly to provide alignment during assembly of the preferred embodiment such that assembly is easy and drops in under the weight of the parts themselves for the matching and mating of the thread thrust relationship between container 14 and thrust handle 6.

FIG. 13 depicts a cross sectional side elevation view of thrust handle 6, plug 7, lid 4, container 14, canister 2, and measurement stand 3. This view illustrates a number of assembly bevel leads such that vertical assembly of the parts may be established with a drop in self assembling system whereby the system self aligns and self assembles under the gravitation weight of its own component parts, or under the weigh of the sums of the component parts which comprise the assembly at the time of drop in assembly sequence. This figure depicts assembly lead 4g and assembly 4h of lid 4, auto flange lead 14g, measurement stand bevel assembly lead 3w, bottle/container assembly bevel/radius lead 14v, and measurement stand leads 3x and 3y. In an alternative embodiment, a curvilinear canister sealing rim 2o can make sealing contact with curvilinear soft dual shot soft seal 4a12 which has been affixed to lid 4 during molding at curvilinear lid sealing surface 4a13. The canister and lid leads effected by the curvilinear shape of the sealing surface contours 4a12 and 2o, there between interposing the soft dual shot seal 4a12. Curvilinear lead 4a14 has a leading dimension from its curve which is closest to the centerline, and its curve which is furthest from the centerline. Curvilinear canister lead 2p has a lead dimension from its curve closest to the centerline and its curve which is furthest from its centerline. Lead 4a14 and lead 2p are shown in FIG. 13. Each of the leads, 4g, 4h, 4a14, 14g, 3x, 3y, 3w, 14v, and 2p also have a height which may be modified to further optimize the ease of assembly of the preferred embodiment 1, as each of the seals and contact points of the preferred embodiment herein defined assembly in sequence. Sequence for the purposes of this application may indicate that the parts assemble simultaneously or in any particular order as may be defined by the modification of the herein disclosed assembly leads, whether jointly, severally or together. Similarly, each of assembly leads 4g, 4h, 4a14, 14g, 3x, 3y, 3w, 14v, and 2p each have a width and may be further modified for optimization of assembly of the preferred embodiment 1. In addition, these assembly leads assist with the horizontal and vertical alignment of the component parts of the preferred embodiments such that the container threads 14d, and their respective height, pitch, lead, and thrust handle threads 6a, and their respective height, pitch and lead may be aligned properly for engagement during assembly such that sealing and unsealing of the preferred embodiments may be easily achieved to prepare for operations and to carry out the functional and method purposes of the supply chain efficient scenarios described by the instant case. These leads are properly aligned so the canisters, of varying sizes may be easily integrated with the preferred embodiment 1.

Figure 14:
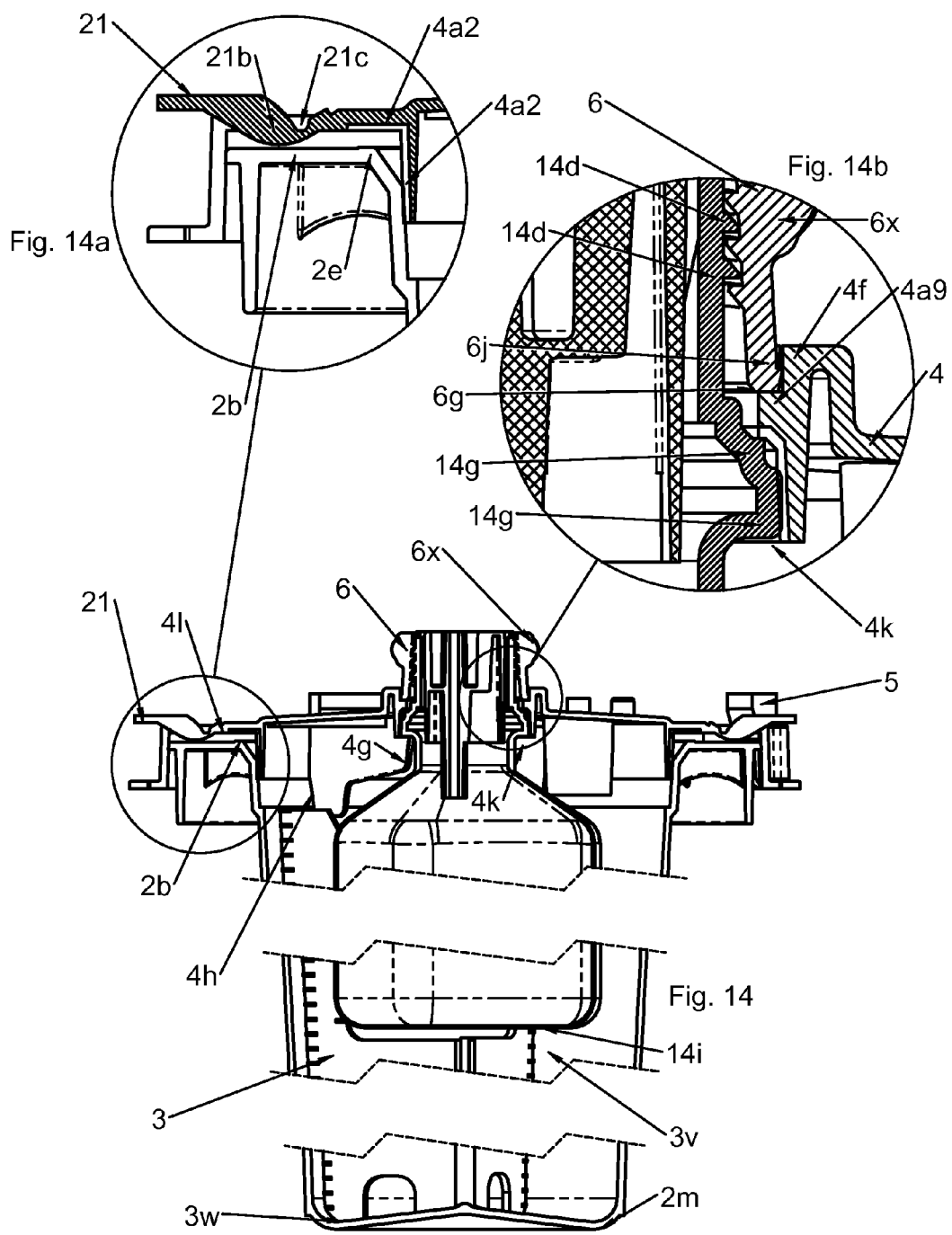
FIG. 14 shows a cross section of the preferred embodiment.

FIG. 14 is a cross sectional cutaway view of the preferred embodiment.

FIG. 14a is substantially similar to that of FIG. 12a.

FIG. 14b is substantially similar to that of FIG. 12b.

Figure 15:
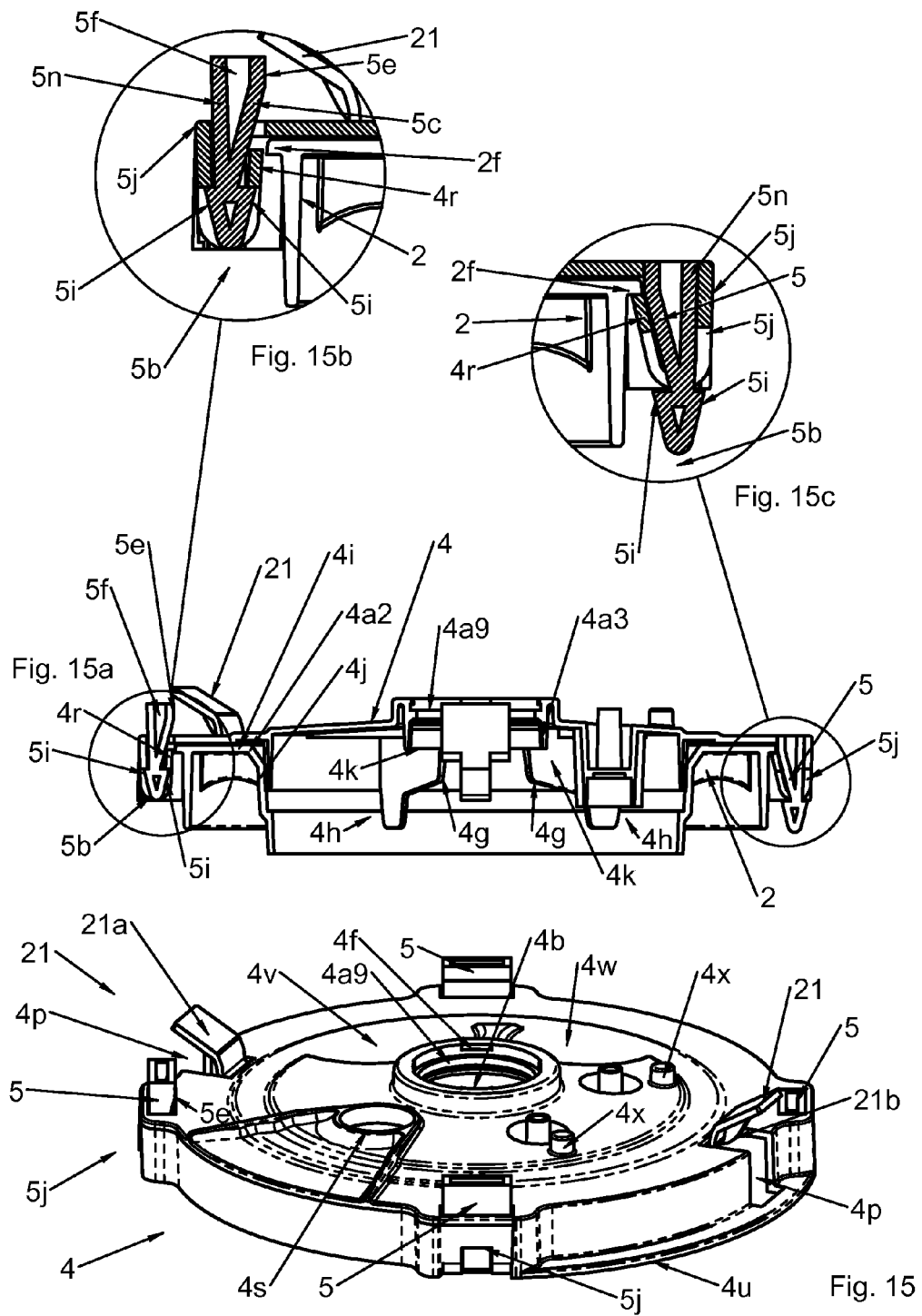
FIG. 15 shows a top perspective view of lid 4.

FIG. 15 shows details of lid 4.

FIG. 15 shows finger lift rim 4u, and four captured locks 5, jacking lever cutout slot 4p, first and second jacking lever 21, first and second jacking keel 21b, first and second jacking lever thumb push surface 21a. Also shown is bottle slot 4b, bottle cap cutaway 4w, spider cap cutaway 4v, pour spout 14s which corresponds with spider plug 8s.

FIG. 15a is a cross sectional view taken at cross section center of two of the captured locks 5, through its center. Detailed here are dual shot soft seals 4a2, 4a9 and 4a3. Soft seal bottle lid are 4k, bottle lid leads 4g, lid/canister leads 4h, jacking lever 21, flat horizontal canister lid seal surface 4i. On the left side of the drawing captured lock 5 is shown in its upright unlocked position showing lid spring lock 4r juxtaposed to canister hook 2f in its resting position. To the right of the FIG. 15a, second captured lock 5 is shown in its down and locked position with the body of lock 5 having pressed lid lock 4r into an interference fit position under canister hook lip 2f. The first lock 5 on the left side of the view the molding slot 5f of lock 5 is shown as well as the lock advancing body 5e is shown.

FIG. 15b is a detailed blow up of the left circle as shown in FIG. 15a, as seen 21 depicts the jacking lever. Lock 5 is depicted by its molding slot 5f, its back side 5n, slot back lock support 4a11 of lid 4, retaining hooks first and second, 5i, lock finger push up bottom 5b, canister 2, lid spring lock 4r, lid hook lift 2f, spring lock push ramp 5c, and spring lock set surface 5e. This figure depicts the captured lock 5 in the upright position, also shown is that it is retained by the interference dimensional fit between lock retention barbs 5i as they are held in place by slot push back 4a11 and spring lock 4r. Lock 5 is assembled to lid 4 by pressing lock 5 down into slot 4q of lid 4. Spring lock 4r springs out and allows first and second retention barbs 5i of locks five to snap into place below spring lock 4r. Spring lock 4r and slot push away surface 4a11 co act together. It is also noted that lock ramp 5c and set surface 5e are positioned towards the center of lid 4 as it is snap assembled into slot 4q.

FIG. 15c is a blow up detail of the right blow up circle as depicted FIG. 15a. FIG. 15c shows the captured lock in a downward locked position. It is shown when the captured lock is pressed downward such that lock top 5a is substantially flush with the surface with lid 4 as shown. Lock spring push ramp 5c pushes lid spring lock 4r which has been juxtaposed to canister rim 2f, which in turn causes an interference fit and locks lid 4 to canister 2 for safe transport of the preferred embodiment 1. As lock 5 is pressed down and lid spring lock 4r resists locking translation under canister hook lip 2f, lock back 5n is stabilized by lid lock support back at 4a11.

Figure 16:
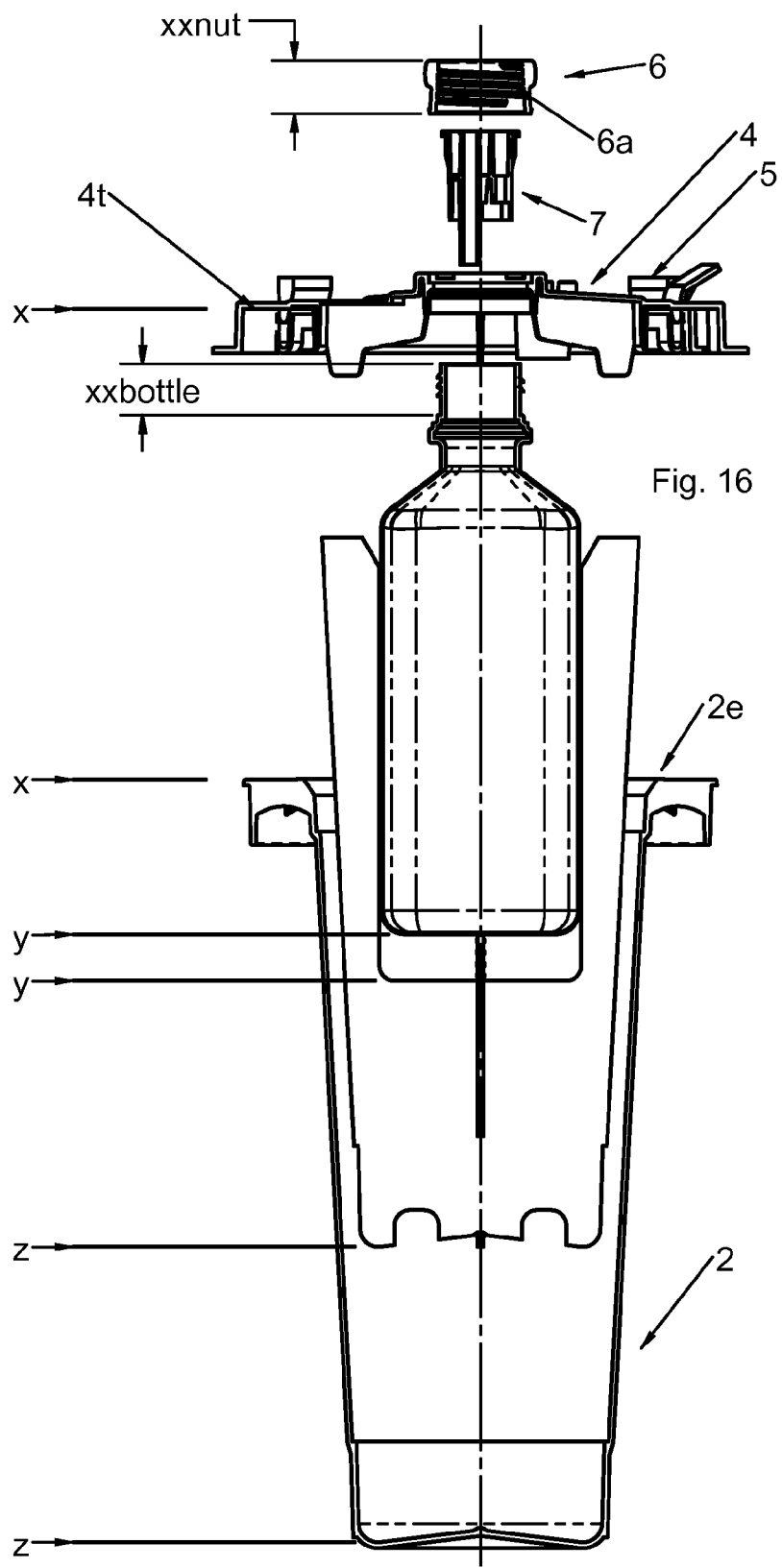
FIG. 16 shows an exploded cross section view of the preferred embodiment of sheet 13 depicting horizontal special relationships of the sub-assembly. This view details specific assembly contact points that are important relative to the clockwise and counterclockwise thrust orientation action of thrust 6 relative to its imparting its thrust onto container 14. XX-nut depicts a thread height of thrust 6, XX-bottle depicts a thread height of bottle thread 14d. When thrust 6 is fully orientated in clockwise orientation as defined in FIG. 3, FIG. 4b, FIG. 5b, FIG. 6b, FIG. 7b FIG. 12b, FIG. 14b, FIG. 18, FIG. 20, FIG. 21, & FIG. 22 and well as would be in FIG. 1, dimension XX-nut and dimension XX-bottle substantially overlap dimensionally and or are dimensionally superimposed. When thrust nut 6 is rotated fully in its counterclockwise orientation dimension XX-nut and dimension XX-bottle un superimpose vertically and create a thrust unsealing dimension expansion comprising the sum of dimensions XX-bottle, and dimension XX-nut.

FIG. 16 is an exploded assembly view of canister 2, measurement stand 3, container 14, lid 4, lock 5, plug 7 and thrust handle 6. Also detailed are stack datum's x showing the lid and the surface seal 2e of canister 2, which defined a mating sealing surface between the lid 4 and canister 2. Also shown are y and y, the upper y showing the container bottom 14i and the stand bottle slot rest surface 3v of said stand. Also shown are z and z, the upper z showing the bottom of measurement stand contact surface 3y and the lower z showing the bottom of the inside 2n of canister 2. As assembled in the sealing position, plug 7 and bottle 14 seal at dual shot bottle plug and container throat seal 7f, the container and lid seal at seal 4a3 and the lid/cannier seal at 4a2. It is also noted that these sealing areas make contact with their respective contacting parts in a substantially horizontal relationship such that when the parts are assembled as such is shown inn FIGS. 21 and 22 among other things, vertical and horizontal relationships remain substantially accurate enough such that handle thrust threads 6a of thrust 6 properly engage container thread 14d of container 14. It is also important to note that the assembly bevel leads as described in FIG. 13, cooperate in a sequence to assist in the vertical and horizontal alignment of thrust thread 6a and container thread 14d. It is also important to note that these leads are arranged and have the structuration to align said threads such that as each lead self engages in sequence, each sequential lead component assembly the distance between the centerline and the point of center of each of these lead has cooperative sutrcutration such that, the leads effectively center and align thread 6a with 14d. It is also important to note that xx-nut defines a thread height of 6a, and xx-bottle defines a thread height of 14d. It is also understood that thread height xx-nut of 6a and thread height xx-bottle 41d may be threaded and unthreaded and vertically superimposed height wise, and create an excursion distance being defined by a clockwise sealing thrust and a counterclockwise unsealing thrust, effecting excursion distance which may equal the sums of the thread heights xx-nut and xx-bottle. The thrust handle contains the potential to impart a force through handle thrust 6, which is very easy to turn yet imparting a significant sealing and unsealing thrust. At sealing area 4k, and at seal 4a2, and at counter clockwise unsealing thrust, the thrust excursion distance between container 14 being the sum of xx-nut and xx-bottle, and an unsealing force at x and x contact areas at dual shot seal 4a2 and also bottle lid sealing area 4k at soft dual shot seal 4a3 through a counteracting contact at container stand yy and stand canister contact zz.

Figure 17:
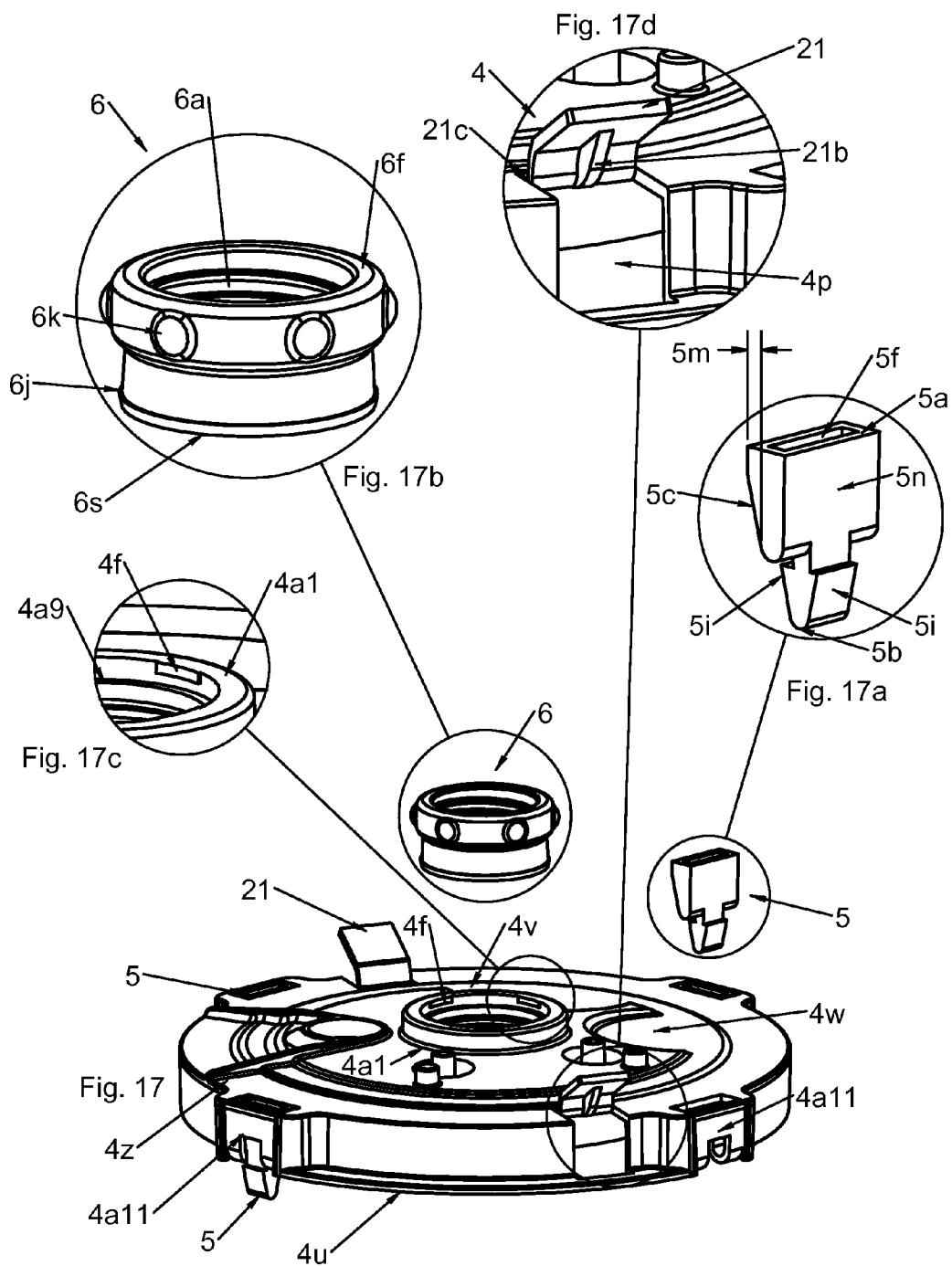
FIG. 17 is a top perspective view of lid 4.

FIG. 17 is a top perspective view of lid 4 showing finger lift rim 4u, one of four locks 5 in the down locked position, lock push back slot 5j of locks slot 4q, shown in two of four places, pour spout fluid guides 4z, locks 5, leveraging ramp 21, lid hook catch and thrust handle retaining hook k4f, spider cap boss 4a1, spider cap cutout 4v, container cap cutout rest 4w.

FIG. 17a shows a blow up detail of lock 5. Shown here is lock 5 bottoms 5b, a finger push up area, first and second retention barbs 5i, lock back 5n, spring lock push ramp 5c, molded in lock slot 5f, lock top 5a, 5m depicts a spring lock push distance.

FIG. 17b is a blow up of handle thrust 6 showing thread 6a, thrust top 6f, thrust retaining rim 6j, thrust bottom 6g, finger friction bumps 6k.

FIG. 17c is a blow up detail of the features of lid boss 4a1 and its handle thrust 6 retaining features. Show in the blow up of 17c, is lid boss 4a1, hook catch thrust retaining hooks 4f, and sealing thrust bearing surface 4a9.

FIG. 17d is a blow up detail of leveraging jack 21 detailing push off contact keel 21b showing lid 4, flexion detent 21c of lid 4, and leveraging jack cutout 4p.

Figure 18:
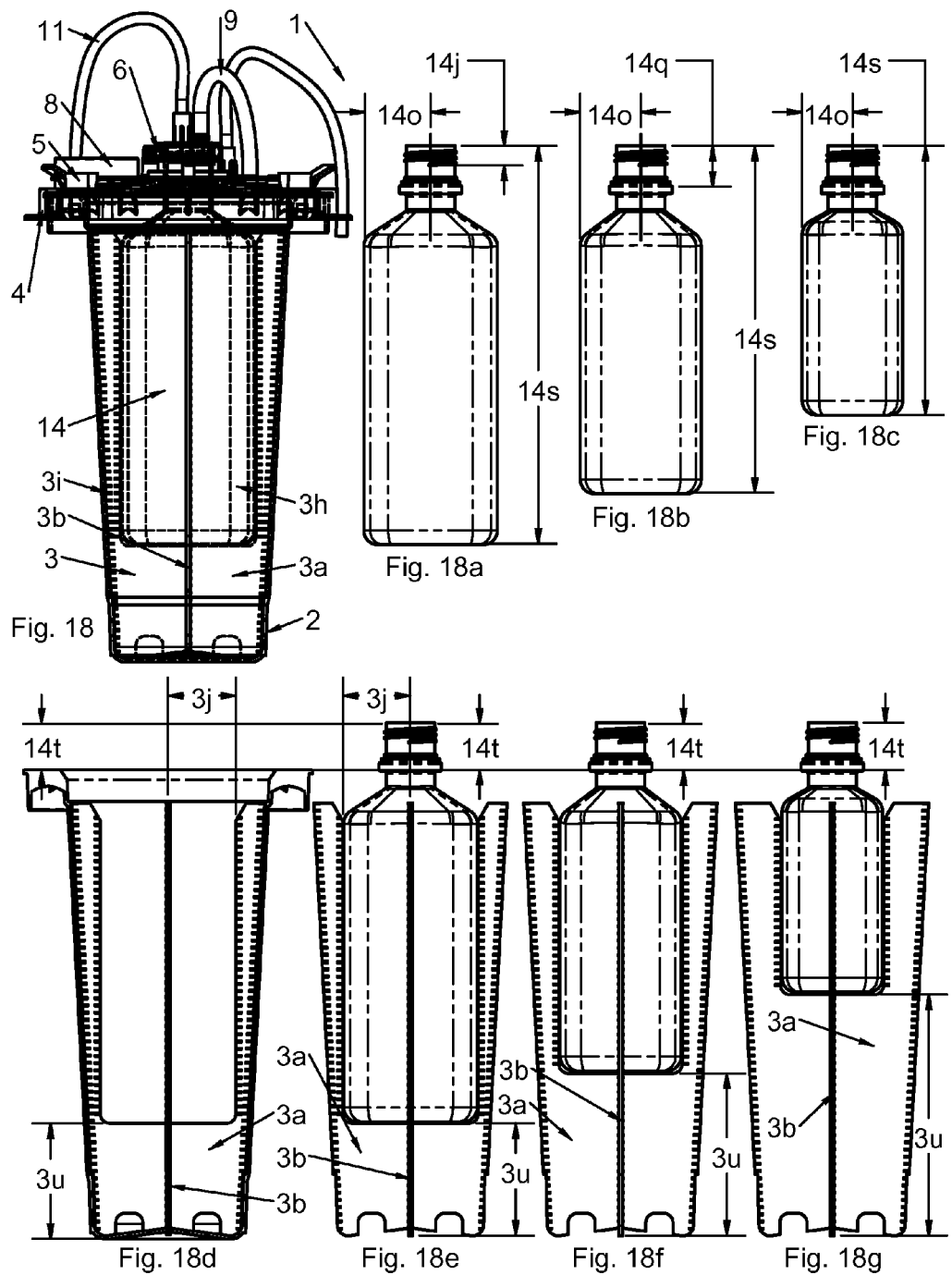
FIG. 18 shows the side elevation transparency view of the preferred embodiment of FIG. 1 in a different rotation view, and in horizontal alignment aspect with respect to different container sizes of FIGS. 18, 18a, 18b, & 18c.

FIG. 18 shows a transparency view of the preferred embodiment 1, detailing patient hose 11, transfer hose 9, thrust handle 6, spider cap 8, lock 9, lid 4, container 14, measuring stand indicia, 3i, container measuring indicia 3h, measuring stand 3, comprising the subassembly components 3a and 3b of stand 3, canister 2.

FIG. 18a shows thread height 14j of thread 14d, distance between the centerline to the flat side of container 14o.

FIG. 18b shows the distance form the assembly centerline from the flat side 14o of container 14, the 14q which is the height distance from seal flange 14g of container 14 to the top of container 14h, the distance form the top 14h of container 14 to the bottom 14i of container 14.

FIG. 18c shows the distance 14o from assembly center line to the flat bottle side 14o of bottle 14 as well as a bottle height 14s showing a distance from bottle top 14h to bottle bottom 14i.

FIG. 18d shows a distance 14t depicting a measurement from the sealing rim 2e of stand 3 to the top 14h of container 14, measurement 3j defines a distance between the assembly centerline and the inside wall 3j of measuring 3 the inner pillar edge shown at 3e. Also defined is measuring distance 3u which defines the distance between the bottom measuring stand 3y and the bottle contact surface 3v of stand 3 as assembled comprising 3a and 3b.

FIG. 18e shows a measurement from the assembly centerline to measuring stand inside pillar edge 3j. Also shown is the height distance 14t defining the distance between bottle top 14h and horizontal canister seal surface 2e. Measuring stand parts 3a and 3b are shown assembled perpendicularly in the vertical plane with respect to each other, and distance 3u defines substantially similar features as found in FIG. 3d.

FIG. 18f substantially similar bottle 4p, 4h, sealing rim 2e, dimension at 15t as well as a substantially larger dimension 3u defining a distance 3u between measuring stand bottom 3y and bottle contact surface 3v and FIG. 18 depicts the substantially the same measuring distance 14t defining the top of bottle 14h and horizontal canister sealing surface 2e and showing dimension 3u from the bottom of stand 3 at 3y to the bottle contact surface 3v as yet being again greater.

FIG. 18 through 18g define a preferred embodiment system 1, which may be provided with a first, second and third container/stand combination to accommodate the collation of fluid waste in various container sizes, and volumes, and shapes. Third, fourth, fifth, and possibly more various sized and shaped containers may be made with similar thread height as shown in 14j with respect to the top of bottle 14h and the bottom of thread 14d as well as shown in FIG. 18d, a substantially similar distance between flange 14g and bottle top 14h as shown at 14q, bottle height distance 4s of FIG. 18 through 18c correspond in structuration differential distance 3u as depicted if FIGS. 18 thorough 18g so that substantially similar bottle thread height xx-bottle as defined in FIG. 16 may be similar yet accommodated by the preferred embodiment 1, irregardless of volume, size shape etc, with respect to different 3u distances as defined in FIG. 18d, e, f, & g. In sheet 18 of 23 it is shown how very high volume production containers of various volumes, shapes and sized may be made with a common thread area, a common sealing area such as thread area 14d and thread flange 14g, as well as common sealing dimensions, and common assembly contact sealing and unsealing dimensions allow integration of a plurality of container volumes and sizes into the preferred embodiment, by the modification of a measuring stand 3 as shown in sheet 18. The modification of measuring stand 3 allow for various bottle volume sized to be embodied by the preferred embodiment whereby a thrust handle provides a significant sealing and unsealing thrust to a plurality of containers having a common thread height area and a common sealing area.

Figure 19:
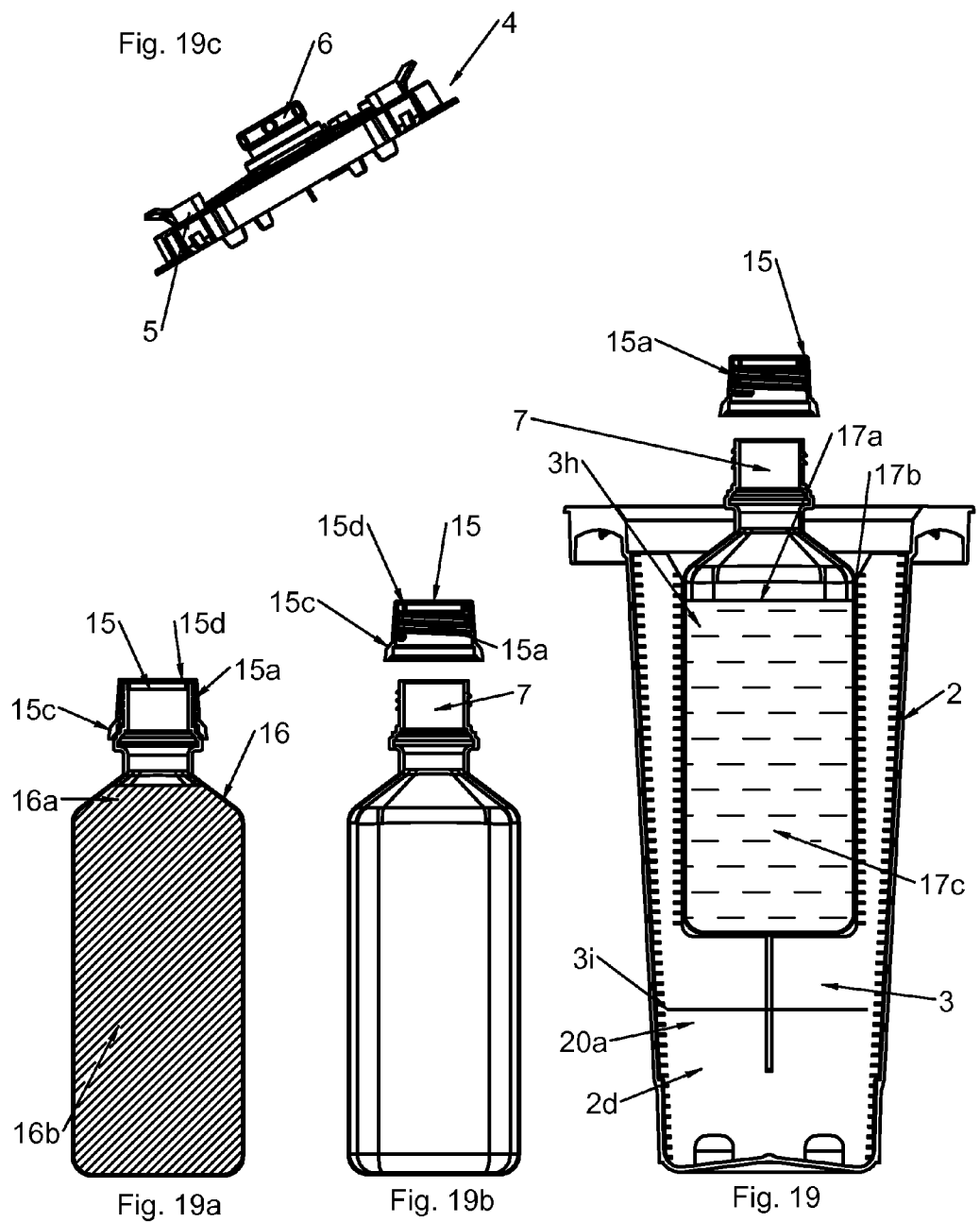
FIG. 19 is a side elevational cross section of the preferred embodiment having lid 4 removed. Waste material has been vacuum drawn (suctioned) into the container and cap 15 is shown in position for ready placement onto bottle 14 sealing in the contaminated waste. This view depicts lid 4 as having the associated vacuum draw hoses/tubing removed thread 6a and thread 14d having been disengaged, thrust handle 6 may be used as a handle, to be held in one hand to hold lid 4 in said one hand, while lid 4 occupies said one hand of an operator, an exchange operation may be carried out with the other hand whereby cap 15 is removed from cutout 4v of lid 4, cap 15 may then be threaded onto bottle 14 while being held in the measurement stand 3, sealing the container. This provides an easy way to seal contaminated waste into container 14 without having to handle or transfer the container 14 while it is unsealed and full of contaminated biological waste fluid material. Container 14 can then be easily removed and another empty container such as in 19b can be placed into measurement stand bottle slotas shown in FIG. 19, and then lid 4 may be placed onto canister 2 in fairly smooth ergonomic fusions.

FIG. 19 is a cross section of the preferred embodiment having lid 4 removed. FIG. 19 shows an improved and efficient human factors and ergonomic sequence for an operator such that one hand may pick up lid 4 by thrust 6 and carry out the operation of changing out the container 14 having waste material therein disposed, and replacing it with a empty container using one hand. Bottle 14 contains waste material. 17a is placed within lid 2 making contact with stand 3 at stand location 3v and bottle bottom 14i. Lid 4 has been removed. Also for illustration, canister fill line 20a shows the potential of overflow of waste material into the canister housing area. 3h is shown as indicia measuring the amount of waste material in the bottle, and 3i shows indicia on stand 3 showing the potential amount of the sums of the material both in the bottle and the canister at 3i. It is noted that although the bottle in FIG. 19 is not completely full the indicia measurement at 3i would be useful if first the bottle was full and then there was overflow. Also shown is throat area, plug 7, bottle cap 15 with bottle cap thread 15a. In this view the preferred embodiment has been utilized to collect waste in a fluid enclosing bottle/container. The hoses/tubing is shown removed from lid 4, thrust handle 6 has been used to unseal the system using counterclockwise rotation imparting distraction excursion forces initiated by the engagement of bottle threads 14 and thrust thread 6a. Handle thrust 6 may be held in one hand by the operator as depicted in 19c (hand not shown), cap 15 has been removed from cap cutout 4w of lid 4 and disposed to re-seal waste 17a in container 14. Once cap 15 is completely tightened onto sealing bottle 14, the operator may lift said bottle out of the preferred embodiment with one hand (the free hand) and while still holding lid 4 in the other hand, place a new empty bottle 14 as defined in FIG. 19b into stand 3 all of which may be carried out with one hand while the other hand holds lid 4. Lid 4 may then be placed back onto the canister to holding handle thrust 6 and thrust 6 may be oriented through a clockwise excursion thusly using forces emanating forces from contact between thread 6a and 14d to fully seal the bottle flange 14g with lid at sealing area 4k at seal 4a3. Full clockwise orientation of handle thread 6 superimposes in vertically dimensionally thrust thread xx-thrust and xx-bottle as defined in sheet 16 allowing superimposing of thread 6a and 14d closing the sum of the distances of thread height 14j and thread height 6b each having a cooperative height thread angle pitch and lead, to allow for captive structuration to align the sums of the heights as they are substantially superimposed and are substantially reduced to the one half of said height sums. This clockwise rotation allows for a dimensional stack up referencing sheet 16 such that canister sealing rim 2e and seal 4n may come into full seal contact, the bottom of bottle 4i and the bottle rest surface 3v and the measuring stand 3 has slight gap in the system and the system may be fully sealed at soft dual shot seal 4a2 and 4a3.

FIG. 20 shows another potential embodiment of unsealing lid 4 form canisters 2. In this view thrust 6 is left untouched and finger lift flanges, first and second 4u are lifted up while first and second jacking lever 21 are pressed down by thumb pressure separating lid 4 and canister 2.

Figure 21:
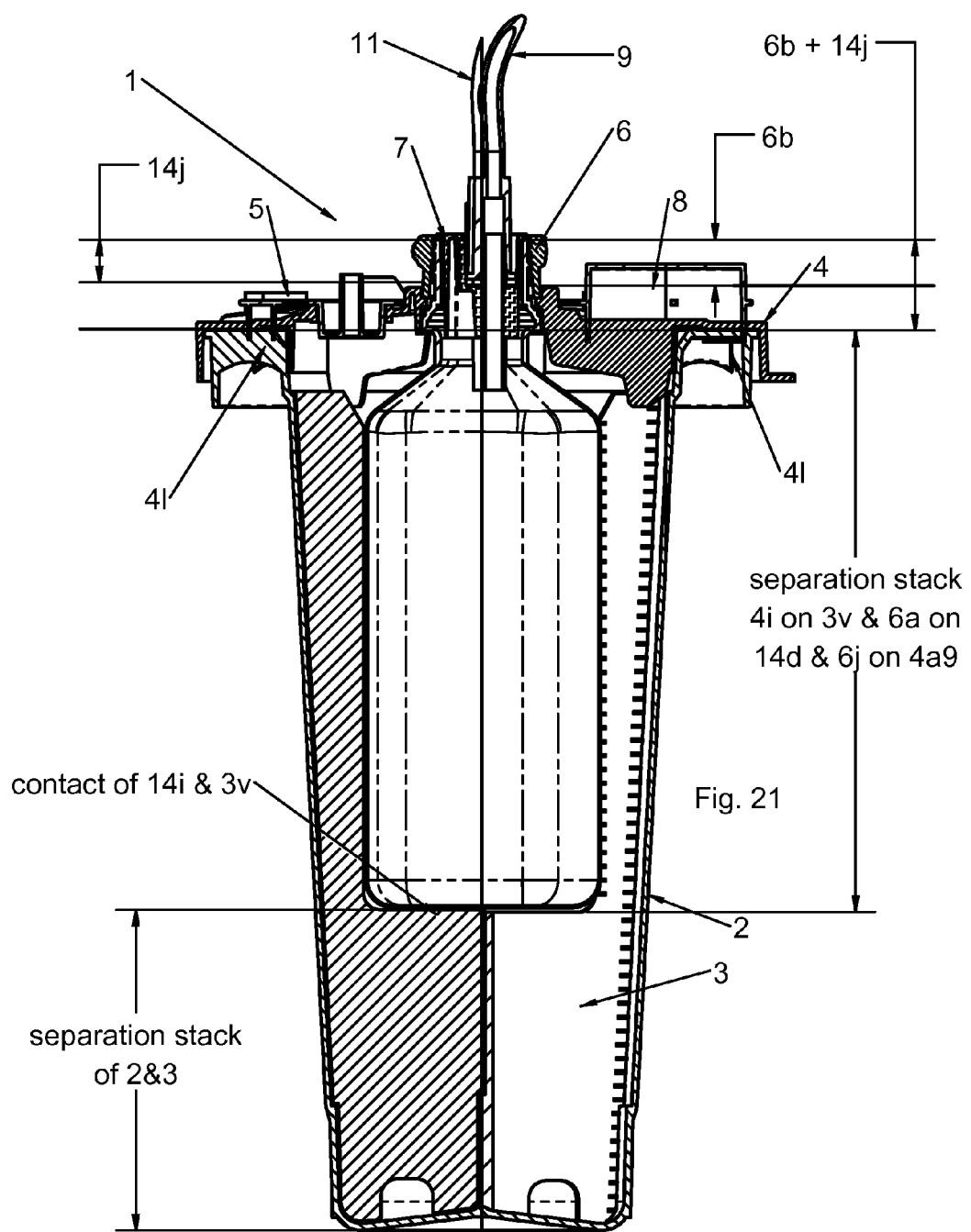
FIG. 21 defines the component's contact stack dimensions that operate under counterclockwise orientation of thrust handle 6.

FIG. 21 shows contact stack of the components that are in structuration during sealing and unsealing of the preferred embodiment. Shown here are measurement stand 3, canister 2, lid 4, lock 5, thrust 6, and spider cap 8. FIG. 21 shows the sums of the thread heights of bottle 14 and thrust 6, and further explains the sums of the thread heights providing separation excursion distances between lid 4 and canister 2 as explained in FIG. 16. 14j defines a bottle thread height. 6b defines a thrust thread height. 6b+14j defines the sums of the thread heights 6b and 14j, separation stack up dimensions of canister 2 an did 3 is shown by horizontal line further defining contact of the bottle bottom 14i and slot bottom 3v of stand 3. Also shown is a vertical separation stack dimension defining a bottle stand contact between canister lid contact dimension which further defines a separation of stack up dimensions of 4i on 3v and 6a on 14d, and 6j on 4a9.

Figure 22:
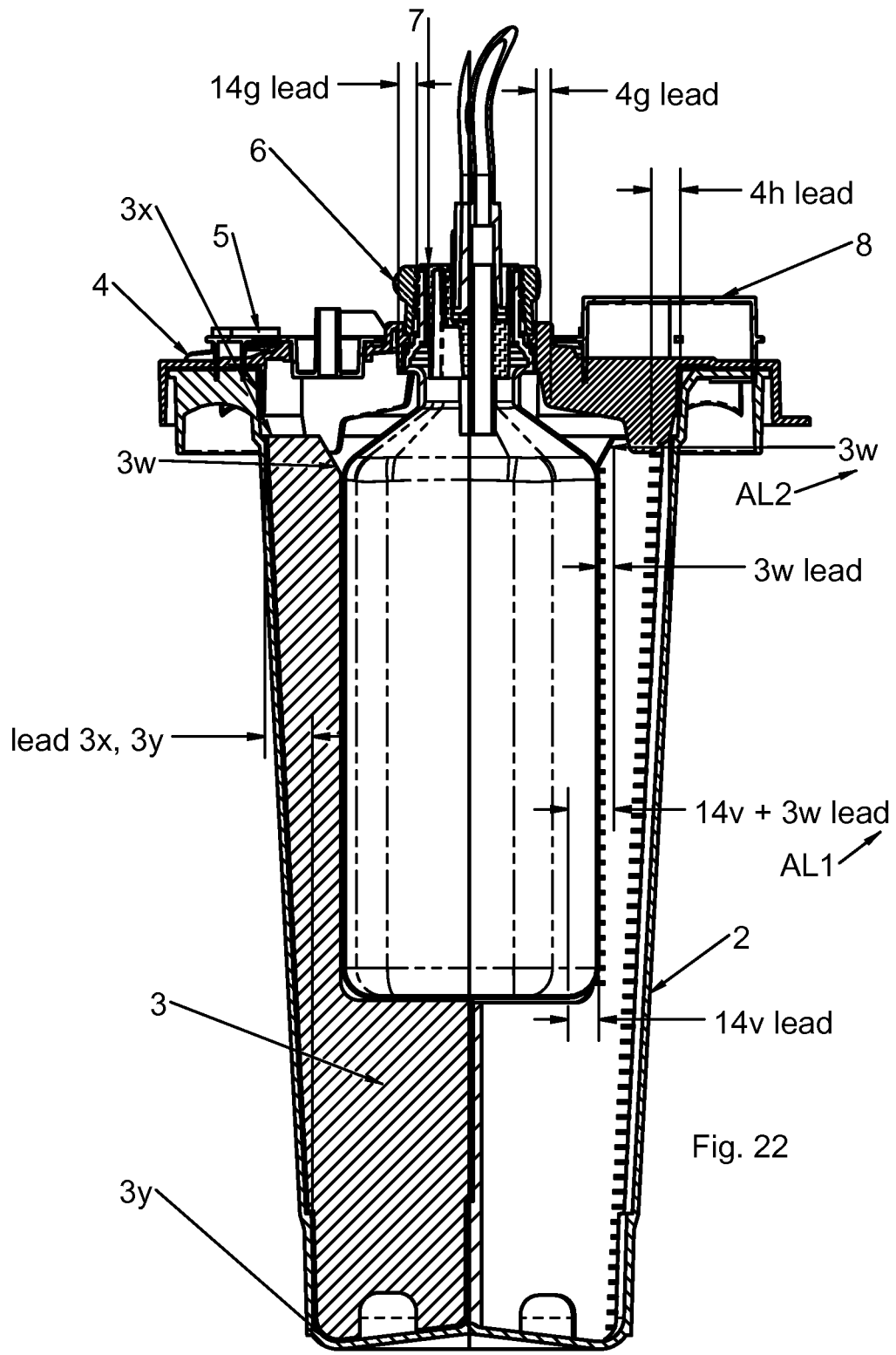
FIG. 22 further defines the vertical leads of the various parts defined in sheet 13 however in a cross sectional view of the assembly of the preferred embodiment.

FIG. 22 further shows the assembly leads defining an easy to use assembly structuration between canister 2, measuring stand 3, bottle 14, lid 4, to further assit in the proper alignment of a bottle thread and a lid thread and sealing surfaces 4a2 and 4a3 as well as sealing area 4k. Also shown is plug 7. Assembly lead 4g allows easier assembly and vertical and horizontal alignment of bottle 14 and lid 4. Assembly lead 4h allows easier vertical and horizontal alignment of lid 4 and canister 2. Another helpful lead would be to have the mating surfaces and associated seal to be curvilinear shaped having corresponding mating seal surfaces having a vertical and horizontal lead from the portion of the curves which is closest to the centerline to the portion of the curves furthest from the centerline. This particular lead would allow a greater slop in assembly and disassembly as well as shorter vertical friction dimension required to unseal lid 4 from canister 2. Leads 4g and 4h are defined by a plurality of leads as they are built into a plurality of vertical wall mold support struts providing strength to the lid during high negative pressure. Also shown is lead 14v on the bottom corner of container 14 and lead 3w which is a cutout bevel of the tops of each of the four measurement stand pillars of components 3a and 3b of stand 3.

These leads all work together to define easier drop in assembly for various bottle sizes to be integrated into the preferred embodiment and are further defined by the use of a plurality of measuring stands 3 each accommodating the size and shape to match threads 6a and 14d.

Figure 23:
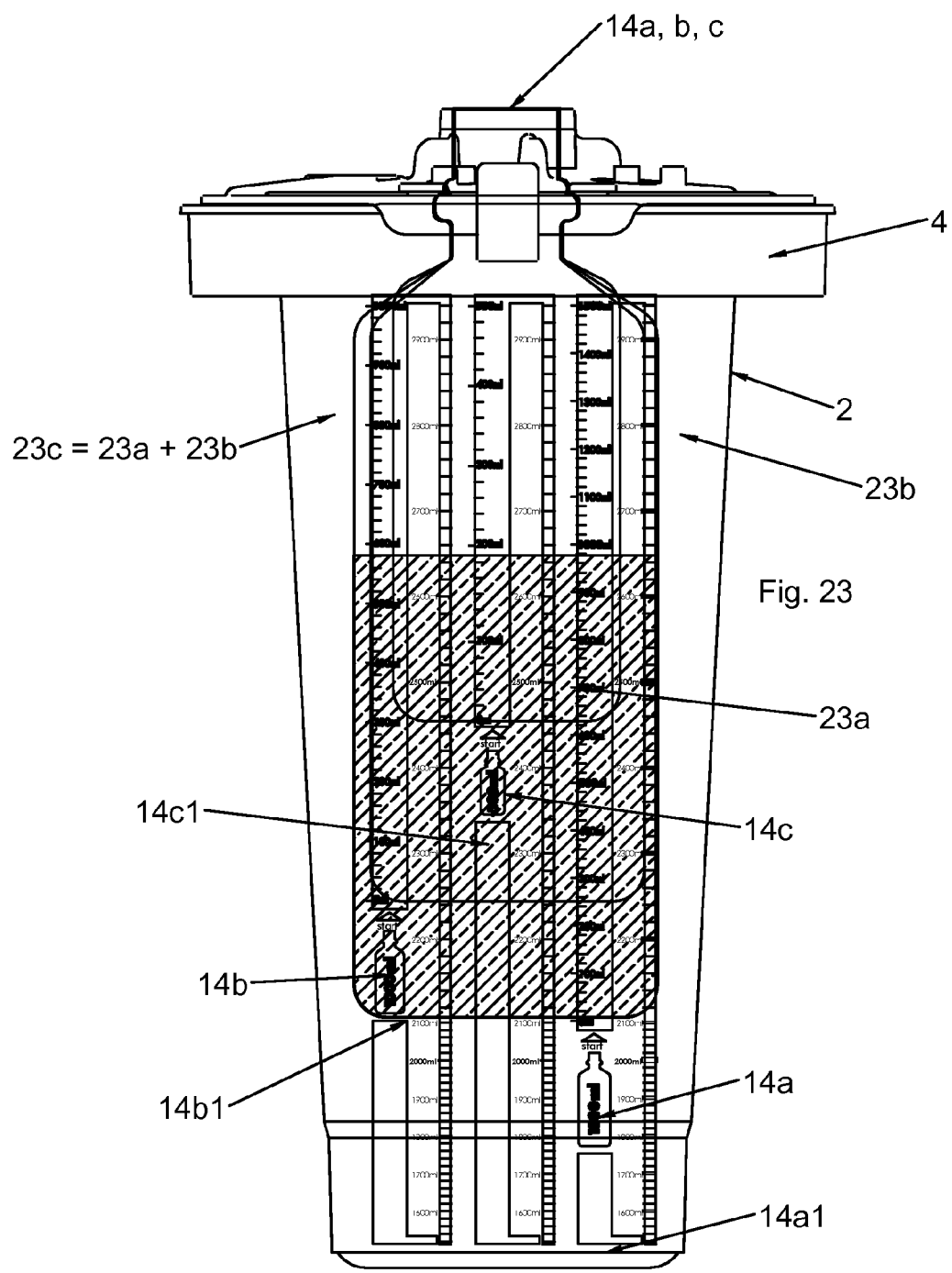
FIG. 23 is a side elevation of an alternative means of indicia depicting a three in one fluid volume measurements system laid out on the outside of a canister 2 whereby several different size bottle volumes can be measured from the outside of a single canister body. The different bottle volumes fit in and are measured off of the same canister body such that for each size there is an indicator of volume in the container and in the event of overflow from the bottle into the canister, measurement from each container volume size that indicate both the volume in the bottle and the overflow volume which has been drawn into the canister, by showing in one vertical measurement strip the volume equivalent to volumes associated with the waste collected in the bottle plus the overflow amount in canister. The measurement amount in the canister, at the bottom of the measurement strip begins with the volume of the bottle volume which is inside the canister. For example, if the measurement strips on the outside of the canister depict that there are three volumes of bottles associated with this canister, then there may be a picture of the bottle volume and the numbers for each respective measurement strip at the bottom of the canister which begins at a volume number that represents the amount of fluid which has already been drawn into the bottle, for the volume of the particular bottle in the canister at that time.

FIG. 23 shows side elevation view of indica placed on the outside of the canister housing.

This view shows six fluid measurement fluid level areas each measuring the level of fluid in the respective different container volume sizes plus that volume and the volume which would be in addition to that volume plus the volume of fluid in the canister 2 in the event of overflow from the bottle 14, through transfer hose 9 and into canister 2.

What is claimed is:
1. A supply chain system comprising,
   a) a plurality of separate supplies of materials having been previously egressed from a plurality of differently sized containers,
   b) said pluralities of said differently sized containers having been subsequently retained within a plurality of differently configured spaces inside a plurality of housings,
   c) a plurality of differently configured separate measurement stands confiqured to support said containers during occupancy of said differently configured spaces whereby a plurality of vacuum sources are configured to draw a plurality of vacuum flows out of and into said spaces and said containers along a plurality of vacuum draw paths.

2. A supply chain system of claim 1 wherein said materials include therapeutics.

3. A supply chain system of claim 1 wherein said materials include medicaments.

4. A supply chain system of claim 1 wherein said materials include pharmaceutical preparations.

5. A supply chain system of claim 1 wherein said materials includes formularies.

6. A supply chain system of claim 1 wherein said materials includes irrigating solutions.

7. A supply chain system of claim 1 wherein said materials include medicaments.

8. A supply chain system of claim 1 wherein said materials includes saline solutions.

9. A supply chain system comprising,
   a) a container from which a material has been previously egressed,
   b) a housing configured to retain said container,
   c) a space interposed between said container and said housing,
   d) a plurality of differently sized separate measurement stands configured to support differently sized containers at different times during different said space interpositions, whereby,
   a composite draw path connected to a vacuum source configured to egress and ingress a vacuum flow out of and into said container, said space and said housing during said different space interpositions.

10. A supply chain system of claim 9 wherein said material includes anesthetic agents.

11. A supply chain system of claim 9 wherein said material includes intravenous therapeutics.

12. A supply chain system of claim 9 wherein said material includes formularies.

13. A supply chain system of claim 9 wherein said container is at least in part comprised of thermally laminated sheets.

14. A supply chain system of claim 9 wherein said container comprises a blow molded container.

15. A supply chain system of claim 9 wherein said container comprises a blow fill seal container.

16. A supply chain system comprising,
   a) a container from which a material has been previously egressed,
   b) a housing conditioned to retain said container,
   c) a space within said housing external to said container wherein separate measurements stands of different sizes at different times occupy said space to support containers of different configurations, whereby
   a composite draw path connected to a source of vacuum, said vacuum source configured to draw a reduced pressure away from said container, said housing, and said space at said different times along portion of said composite draw path between a site of waste and said vacuum source.

17. A supply chain system of claim 16 wherein said material includes a therapeutic.

18. A supply chain system of claim 16 wherein said material includes a formulary.

19. A supply chain system of claim 16 wherein said container comprises at least in part thermally laminated sheets.

20. A supply chain system of claim 16 wherein said container comprises a blow molded container.

21. A supply chain system of claim 16 wherein said container comprises a blow fill seal container.

* * * * *

UNITED STATES PATENT AND TRADEMARK OFFICE
CERTIFICATE OF CORRECTION

PATENT NO. : 8,888,753 B2
APPLICATION NO. : 13/348074
DATED : November 18, 2014
INVENTOR(S) : Jack W. Romano and Adam L. Smith Page 1 of 2

It is certified that error appears in the above-identified patent and that said Letters Patent is hereby corrected as shown below:

In the Specification

Column 1, line 31: delete first instance "canister" and insert --canisters-- to read "as canisters and/or....".
Column 2, line 51-52: delete "in" at the end of line 51 to read "example collection....".
Column 3, line 60: delete "container" and insert --containers-- to read "large containers are....".
Column 4, line 57: delete "that" and insert --than-- to read "greater than a....".
Column 4, line 65: delete "=" to read "seals that are not....".
Column 5, line 30: insert --of-- between --collection-- and --waste-- to read "collection of waste....",
Column 5, line 58-59: delete "and is" and insert --as-- to read "known as a closed....".
Column 6, line 2: delete "these" and insert --the-- to read "of the instant....".
Column 6, line 18: delete the second "the" to read "(unnecessary) need....".
Column 6, line 35: delete "solution" and insert --solutions,-- to read "saline solutions, intravenous....".
Column 6, line 57: delete "container" and insert --containers-- to read "Other containers such....".
Column 6, line 60: delete "suitable" and insert --suitably-- to read "function suitably within....".
Column 7, line 21: insert --the-- between --facility.-- and --Present-- to read "facility. The present....".
Column 10, line 25: delete "it" and insert --it's-- to read "dispensing of it's contents....".
Column 10, line 26: insert --in-- between --is-- and --position-- to read "is in position....".
Column 12, line 15: delete "show" and insert --shows-- to read "FIG. 5 shows dual....".
Column 12, line 46: delete "show" and insert --shows-- to read "which shows various....".
Column 13, line 57: delete "sows" and insert --shows-- to read "FIG. 14b shows thrust....".
Column 13, line 6-7: delete "special" and insert --spacial-- to read "horizontal spacial relationships....".
Column 14, line 15: delete "and" and insert --as-- to read "FIG. 22 as well....".
Column 14, line 36: delete "a" between --depicting-- and --dimensions-- to read "depicting dimensions....".
Column 15, line 26: delete "slotas" and insert --slots-- to read "bottle slots shown....".
Column 16, line 15: delete "two" and insert --2-- to read "body 2 is shown....".
Column 16, line 34: delete "an" and insert --and-- to read "lock 5, and jacking....".

Signed and Sealed this
Tenth Day of March, 2015

Michelle K. Lee
*Deputy Director of the United States Patent and Trademark Office*

CERTIFICATE OF CORRECTION (continued)

Column 16, line 36-37: delete "hose" at the end of the line 36 to read "vacuum transfer hose 9....".
Column 16, line 63-64: delete "the" at the end of line 36 between --showing-- and --interposing-- to read "showing interposing....".
Column 17, line 25: delete "angles" and insert --angled-- to read "vertically angled canister....".
Column 17, line 33: delete "portinsurface" and insert --surface-- to read "bearing surface 4a9,....".
Column 17, line 45: delete "an hd" and insert --and lid-- to read "canisters 2 and lid 4....".
Column 18, line 12: delete "hot" and insert --shot-- to read "dual shot seal...".
Column 18, line 27: delete "a" to read "is respectively....".
Column 18, line 34: delete "thought" and insert --though-- to read "though bottle....".
Column 18, line 39: delete "sot" and insert --slot-- to read "stand slot bottom....".
Column 18, line 44: delete "6 xs" and insert --6x-- to read "thrust 6x continually....".
Column 19, line 47: delete the first "soft" to read "curvilinear dual shot soft seal....".
Column 20, line 28: delete "are" to read "lid 4k....".
Column 20, line 36: insert --of-- between --view-- and --the-- to read "view of the molding....".
Column 20, line 51: delete "five" and insert --5-- to read "locks 5 to snap....".
Column 20, line 57: insert --in-- between --depicted-- and --FIG. 15a-- to read "depicted in FIG. 15a....".
Column 21, line 13: delete "cannier" and insert --canister-- to read "lid cannister seal....".
Column 21, line 16: delete "inn" and insert --in-- to read "shown in FIG. 21....".
Column 21, line 28: delete "lead has" and insert --leads have-- to read "these leads have cooperative....".
Column 21, line 51: delete "k4f" and insert --4f-- to read "hook 4f, spider cap....".
Column 22, line 21: insert --stand-- between --measuring-- and --3-- to read "measuring stand 3....".
Column 22, line 36: delete "the" between --depicts-- and --substantially-- to read "depicts substantially....".
Column 22, line 52: delete "if" and insert --in-- to read "depicted in FIGS. 18....".
Column 22, line 58: delete "sized" and insert --sizes-- to read "and sizes may....".
Column 22, line 66: delete "sized" and insert --sizes-- to read "volume sizes to be....".
Column 23, line 37: delete "to" between --canister-- and --holding-- to read "canister holding....".
Column 23, line 39: delete "forces" between --emanating-- and --from-- to read "emanating from....".
Column 23, line 41: delete "in" at the end of the line to read "superimposes vertically....".
Column 24, line 3: delete "an did" and insert --and lid-- to read "canister 2 and lid 3....".

In the Claims

Column 26, line 16, claim 16: insert --a-- between --along-- and --portion-- to read "along a portion....".